United States Patent
Lin

(10) Patent No.: US 9,029,669 B2
(45) Date of Patent: *May 12, 2015

(54) CULTIVAR, METHOD FOR DIFFERENTIATING PLANT CULTIVARS, AND METHOD FOR CAUSING EARLIER MATURING OF RICE INDIVIDUAL

(75) Inventor: Shaoyang Lin, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/005,225

(22) PCT Filed: Mar. 18, 2011

(86) PCT No.: PCT/JP2011/056551
§ 371 (c)(1),
(2), (4) Date: Sep. 13, 2013

(87) PCT Pub. No.: WO2012/127559
PCT Pub. Date: Sep. 27, 2012

(65) Prior Publication Data
US 2014/0090109 A1    Mar. 27, 2014

(51) Int. Cl.
*A01H 5/10* (2006.01)
*C12Q 1/68* (2006.01)
*C12N 15/82* (2006.01)

(52) U.S. Cl.
CPC .............. *C12N 15/8262* (2013.01); *A01H 5/10* (2013.01); *C12Q 1/6895* (2013.01)

(58) Field of Classification Search
USPC .............................. 800/320.2, 260, 267, 320.1
See application file for complete search history.

(56) References Cited

U.S. PATENT DOCUMENTS

| 7,566,815 B2 | 7/2009 | Takano et al. |
| 2006/0123507 A1 | 6/2006 | Ashikari et al. |
| 2008/0320611 A1 | 12/2008 | Takashi et al. |

FOREIGN PATENT DOCUMENTS

| JP | 3660967 B2 | 4/2005 |
| JP | 2008-283902 A | 11/2008 |
| JP | 4352102 B1 | 10/2009 |
| JP | 4368391 B2 | 11/2009 |
| JP | 2010-011826 A | 1/2010 |
| JP | 4409610 B2 | 2/2010 |
| JP | 4892648 B1 | 3/2012 |
| WO | WO 03/070934 A1 | 8/2003 |
| WO | WO 2004/044200 A1 | 5/2004 |

OTHER PUBLICATIONS

Takeuchi et al. Breeding Science (2006), vol. 56:405-413.*
Shimizu et al. Breeding Science (1997) 47(Suppl.1), Abstract of 91$^{st}$ Lecture by Japanese Society of Breeding.*
Yamamoto et al. Theor Appl Genet (2007) 115:187-196.*
International Search Report, PCT/JP2011/056551 dated Apr. 19, 2011.
Japanese Office Action, Application No. 2011-513769, mailing date Jun. 14, 2011.
Mayuko Ikeda, et al., "Tashu Ine, Habataki no Ho no Chakuryu Kozo Keisei ni Kakawaru Gnl Oyobi QTL no Pyramiding", Breeding research, Sep. 24, 2010, vol. 12, separate vol. 2, p. 253.
Taiichiro Okawa, "(9) Ko-Biomass Tashusei Suito Chokan Hinshu ga Sonaeru beki Tai-Tofukusei ni Kan'yo suru Kyoku-Kyokan Keishitsu no QTL Kaiseki", Kenkyu Seika Dai 471 Shu 'Genome Ikushu ni yoru Koritsuteki Hinshu Ikusei Gijutsu no Kaihatsu, QTL Idenshi Kaiseki no Suishin', Feb. 20, 2009, pp. 60 to 63.

* cited by examiner

*Primary Examiner* — Medina A Ibrahim
(74) *Attorney, Agent, or Firm* — Carrier Blackman & Associates, P.C.; Joseph P. Carrier; Fulchand P. Shende

(57) ABSTRACT

An object of the present invention is to provide a new rice cultivar that matures earlier than the original cultivar, and a method for causing a rice individual to mature earlier. The present invention relates to a rice cultivar Koshihikari kazusa no. 6 having the cultivar registration application number 25587, a progeny individual obtained by crossbreeding two individuals selected from the group consisting of an individual of the aforementioned cultivar and a progeny individual thereof, and a method for causing a rice individual to mature earlier that comprises replacing a region corresponding to a region containing base number 31,720,064 to base number 31,724,043 of the third chromosome of rice cultivar Nipponbare with a chromosome fragment composed of the corresponding region of rice cultivar Koshihikari kazusa no. 6 or rice cultivar Habataki in the third chromosome of the rice individual.

8 Claims, 8 Drawing Sheets

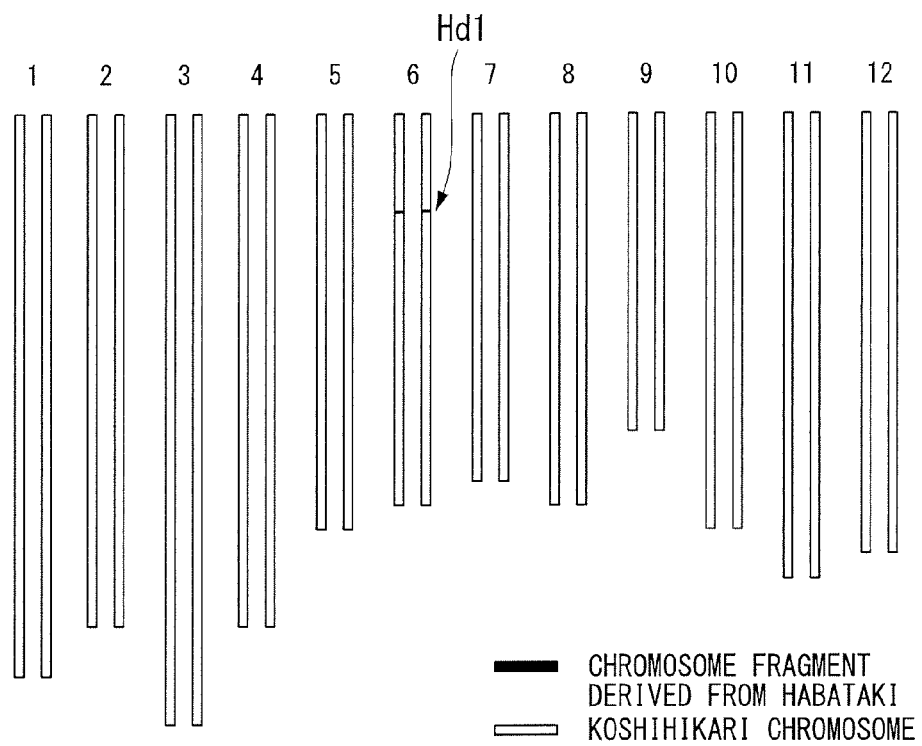
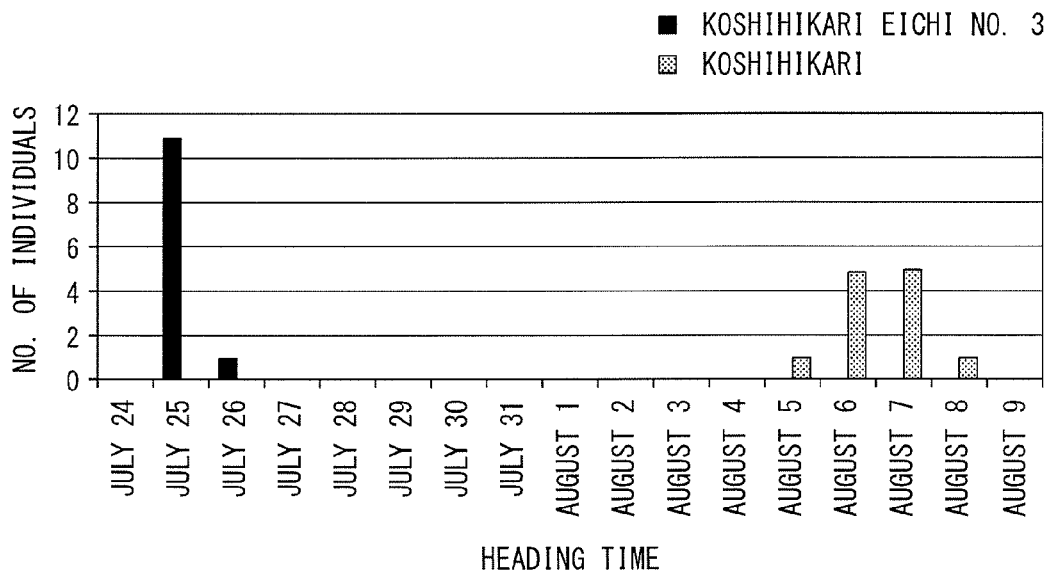

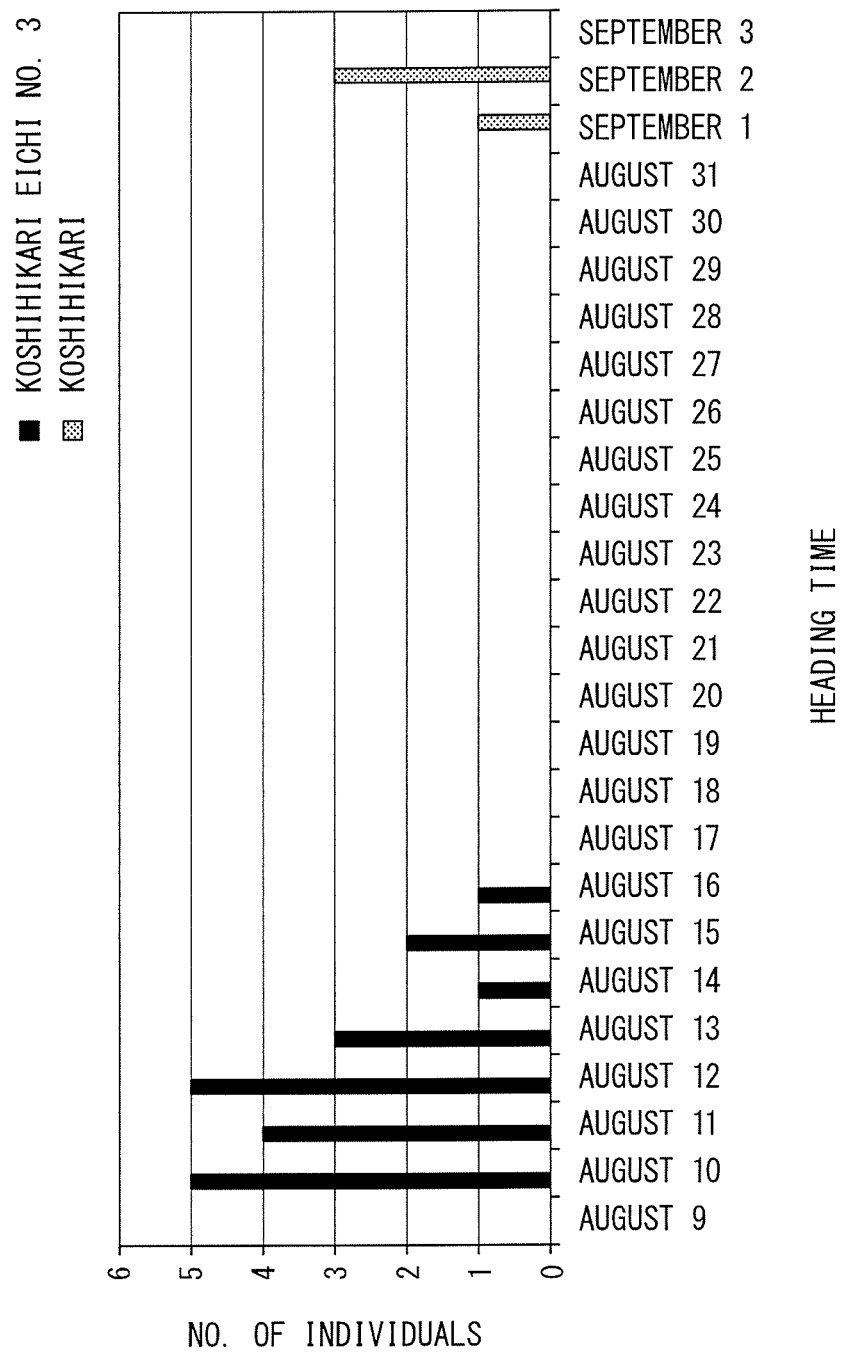

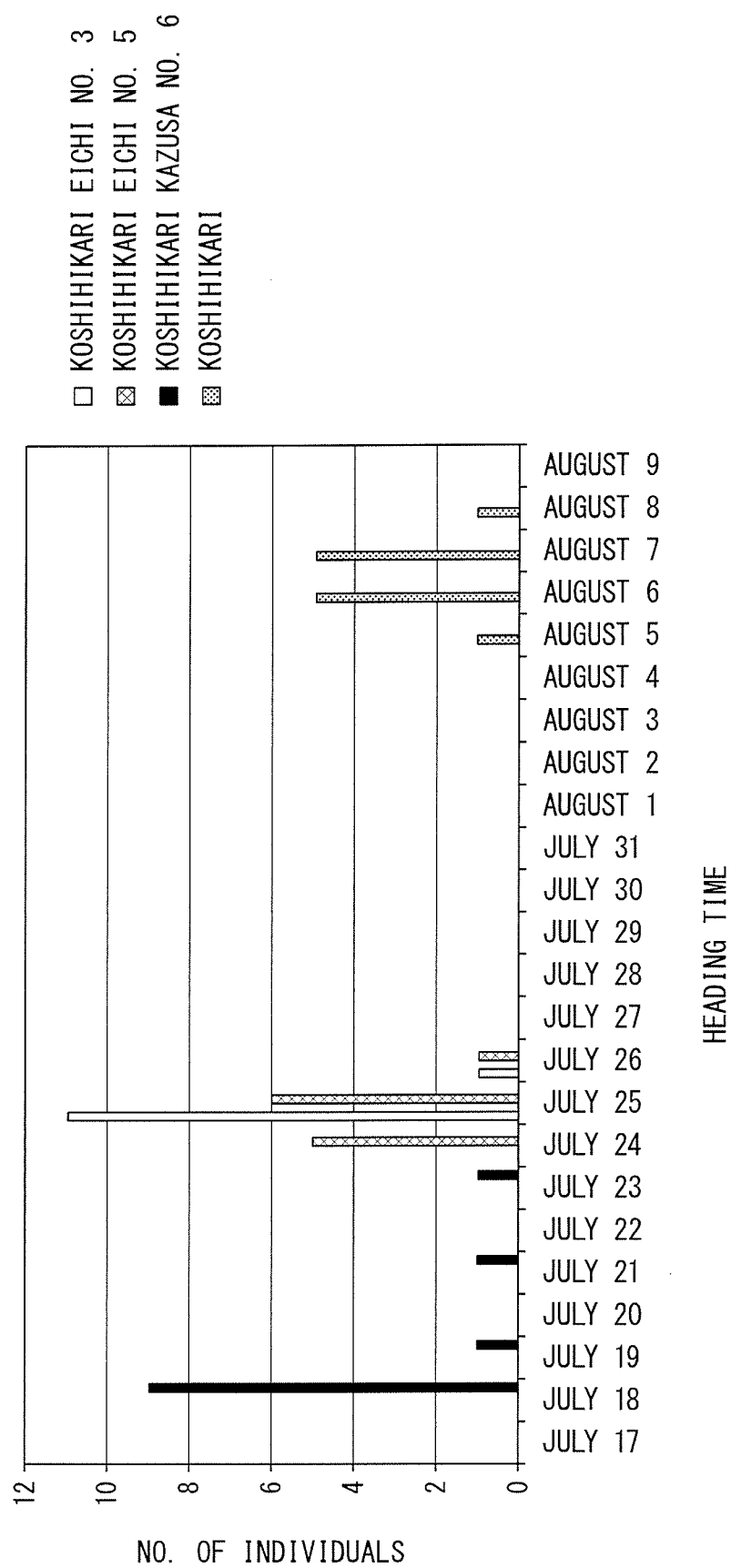

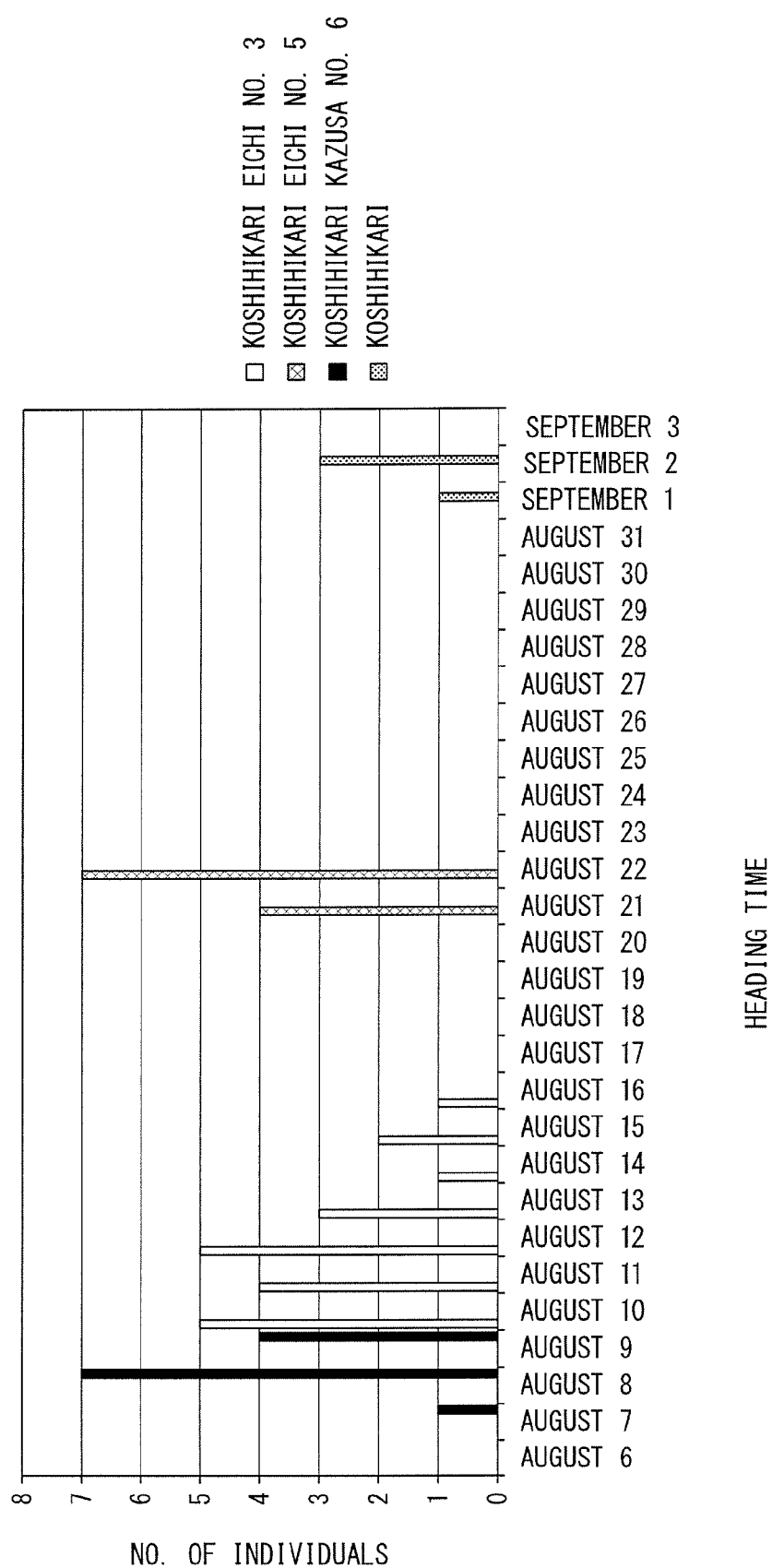

```
                        SEQUENCE LISTING

<160> NUMBER OF SEQ ID NOS: 30

<210> SEQ ID NO 1
<211> LENGTH: 20
<212> TYPE: DNA
<213> ORGANISM: Oryza sativa
<220> FEATURE:
<223> OTHER INFORMATION: DNA marker: Upper Primer of M1-Ac(QTS14)

<400> SEQUENCE: 1
cattcagttc tctcaactgc                                                   20

<210> SEQ ID NO 2
<211> LENGTH: 22
<212> TYPE: DNA
<213> ORGANISM: Oryza sativa
<220> FEATURE:
<223> OTHER INFORMATION: DNA marker: Lower Primer of M1-Ac(QTS14)

<400> SEQUENCE: 2
gagattttcg aaggttcttc gc                                                22

<210> SEQ ID NO 3
<211> LENGTH: 19
<212> TYPE: DNA
<213> ORGANISM: Oryza sativa
<220> FEATURE:
<223> OTHER INFORMATION: DNA marker: SNP Primer of M1-Ac(QTS14)

<400> SEQUENCE: 3
ttcctaaccc agctgtgat                                                    19

<210> SEQ ID NO 4
<211> LENGTH: 20
<212> TYPE: DNA
<213> ORGANISM: Oryza sativa
<220> FEATURE:
<223> OTHER INFORMATION: DNA marker: Upper Primer of M2-Ct (QTS14)

<400> SEQUENCE: 4
aaaacagcca cacctgatcg                                                   20
```

-continued

```
<210> SEQ ID NO 5
<211> LENGTH: 20
<212> TYPE: DNA
<213> ORGANISM: Oryza sativa
<220> FEATURE:
<223> OTHER INFORMATION: DNA marker: Lower Primer of M2-Ct (QTS14)

<400> SEQUENCE: 5
aacatcctct gcttcctcag                                              20

<210> SEQ ID NO 6
<211> LENGTH: 20
<212> TYPE: DNA
<213> ORGANISM: Oryza sativa
<220> FEATURE:
<223> OTHER INFORMATION: DNA marker: SNP Primer of M2-Ct (QTS14)

<400> SEQUENCE: 6
tatcgctagc ctccatttct                                              20

<210> SEQ ID NO 7
<211> LENGTH: 21
<212> TYPE: DNA
<213> ORGANISM: Oryza sativa
<220> FEATURE:
<223> OTHER INFORMATION: DNA marker: Upper Primer of M3-Ag (QTS14)

<400> SEQUENCE: 7
gaatggaatg agccatactc c                                            21

<210> SEQ ID NO 8
<211> LENGTH: 20
<212> TYPE: DNA
<213> ORGANISM: Oryza sativa
<220> FEATURE:
<223> OTHER INFORMATION: DNA marker: Lower Primer of M3-Ag (QTS14)

<400> SEQUENCE: 8
ctgcatctac acgctatacc                                              20

<210> SEQ ID NO 9
<211> LENGTH: 25
<212> TYPE: DNA
<213> ORGANISM: Oryza sativa
<220> FEATURE:
<223> OTHER INFORMATION: DNA marker: SNP Primer of M3-Ag (QTS14)

<400> SEQUENCE: 9
gtgatggaaa agttggaagt ttgaa                                        25

<210> SEQ ID NO 10
<211> LENGTH: 20
<212> TYPE: DNA
<213> ORGANISM: Oryza sativa
<220> FEATURE:
<223> OTHER INFORMATION: DNA marker: Upper Primer of M4-Gc (QTS14)

<400> SEQUENCE: 10
tccatccgat gcagatatcc                                              20

<210> SEQ ID NO 11
<211> LENGTH: 21
<212> TYPE: DNA
<213> ORGANISM: Oryza sativa
<220> FEATURE:
<223> OTHER INFORMATION: DNA marker: Lower Primer of M4-Gc (QTS14)
```

```
<400> SEQUENCE: 11
gtagttatgg tacactcgca g                                              21

<210> SEQ ID NO 12
<211> LENGTH: 21
<212> TYPE: DNA
<213> ORGANISM: Oryza sativa
<220> FEATURE:
<223> OTHER INFORMATION: DNA marker: SNP Primer of M4-Gc (QTS14)

<400> SEQUENCE: 12
gctggggaaa gtgatttcat c                                              21

<210> SEQ ID NO 13
<211> LENGTH: 21
<212> TYPE: DNA
<213> ORGANISM: Oryza sativa
<220> FEATURE:
<223> OTHER INFORMATION: DNA marker: Upper Primer of M5-At (QTS14)

<400> SEQUENCE: 13
acgtggggta cagcactttg a                                              21

<210> SEQ ID NO 14
<211> LENGTH: 20
<212> TYPE: DNA
<213> ORGANISM: Oryza sativa
<220> FEATURE:
<223> OTHER INFORMATION: DNA marker: Lower Primer of M5-At (QTS14)

<400> SEQUENCE: 14
gtcaggaaag ttggaagagg                                                20

<210> SEQ ID NO 15
<211> LENGTH: 24
<212> TYPE: DNA
<213> ORGANISM: Oryza sativa
<220> FEATURE:
<223> OTHER INFORMATION: DNA marker: SNP Primer of M5-At (QTS14)

<400> SEQUENCE: 15
gatctctgac aatatcaaga agct                                           24

<210> SEQ ID NO 16
<211> LENGTH: 22
<212> TYPE: DNA
<213> ORGANISM: Oryza sativa
<220> FEATURE:
<223> OTHER INFORMATION: DNA marker: Upper Primer of M1-Ct (Hd1)

<400> SEQUENCE: 16
gcgaaaagat gaggatgtac ac                                             22

<210> SEQ ID NO 17
<211> LENGTH: 20
<212> TYPE: DNA
<213> ORGANISM: Oryza sativa
<220> FEATURE:
<223> OTHER INFORMATION: DNA marker: Lower Primer of M1-Ct (Hd1)

<400> SEQUENCE: 17
ccgtaggcct ttgtcaagtg                                                20
```

-continued

<210> SEQ ID NO 18
<211> LENGTH: 20
<212> TYPE: DNA
<213> ORGANISM: Oryza sativa
<220> FEATURE:
<223> OTHER INFORMATION: DNA marker: SNP Primer of M1-Ct (Hd1)

<400> SEQUENCE: 18
ctttaatggt ggcttatgtc                                         20

<210> SEQ ID NO 19
<211> LENGTH: 21
<212> TYPE: DNA
<213> ORGANISM: Oryza sativa
<220> FEATURE:
<223> OTHER INFORMATION: DNA marker: Upper Primer ofM2-Ag (Hd1)

<400> SEQUENCE: 19
gaccttcatc tgagatgtga c                                       21

<210> SEQ ID NO 20
<211> LENGTH: 20
<212> TYPE: DNA
<213> ORGANISM: Oryza sativa
<220> FEATURE:
<223> OTHER INFORMATION: DNA marker: Lower Primer of M2-Ag (Hd1)

<400> SEQUENCE: 20
ggaaagtgaa gcagcttctc                                         20

<210> SEQ ID NO 21
<211> LENGTH: 22
<212> TYPE: DNA
<213> ORGANISM: Oryza sativa
<220> FEATURE:
<223> OTHER INFORMATION: DNA marker: SNP Primer of M2-Ag (Hd1)

<400> SEQUENCE: 21
cagcaagctc ctgtccatat tt                                      22

<210> SEQ ID NO 22
<211> LENGTH: 18
<212> TYPE: DNA
<213> ORGANISM: Oryza sativa
<220> FEATURE:
<223> OTHER INFORMATION: DNA marker: Upper Primer of M3-Cg (Hd1)

<400> SEQUENCE: 22
aggcccttgt actggtac                                           18

<210> SEQ ID NO 23
<211> LENGTH: 21
<212> TYPE: DNA
<213> ORGANISM: Oryza sativa
<220> FEATURE:
<223> OTHER INFORMATION: DNA marker: Lower Primer of M3-Cg (Hd1)

<400> SEQUENCE: 23
gtacacaata gttggtgcac c                                       21

<210> SEQ ID NO 24
<211> LENGTH: 19
<212> TYPE: DNA
<213> ORGANISM: Oryza sativa
<220> FEATURE:
<223> OTHER INFORMATION: DNA marker: SNP Primer of M3-Cg (Hd1)

```
<400> SEQUENCE: 24
catgataagg tactcctgg                                                        19

<210> SEQ ID NO 25
<211> LENGTH: 23
<212> TYPE: DNA
<213> ORGANISM: Oryza sativa
<220> FEATURE:
<223> OTHER INFORMATION: DNA marker: Upper Primer of M4-Gc (Hd1)

<400> SEQUENCE: 25
gtatcaatca tgtgatcagt ggc                                                   23

<210> SEQ ID NO 26
<211> LENGTH: 21
<212> TYPE: DNA
<213> ORGANISM: Oryza sativa
<220> FEATURE:
<223> OTHER INFORMATION: DNA marker: Lower Primer of M4-Gc (Hd1)

<400> SEQUENCE: 26
cctaggaatt aggaagcaca g                                                     21

<210> SEQ ID NO 27
<211> LENGTH: 20
<212> TYPE: DNA
<213> ORGANISM: Oryza sativa
<220> FEATURE:
<223> OTHER INFORMATION: DNA marker: SNP Primer of M4-Gc (Hd1)

<400> SEQUENCE: 27
cagccaacat tgagggctct                                                       20

<210> SEQ ID NO 28
<211> LENGTH: 20
<212> TYPE: DNA
<213> ORGANISM: Oryza sativa
<220> FEATURE:
<223> OTHER INFORMATION: DNA marker: Upper Primer of M5-At (Hd1)

<400> SEQUENCE: 28
cttcgtacca tgatgcaggg                                                       20

<210> SEQ ID NO 29
<211> LENGTH: 20
<212> TYPE: DNA
<213> ORGANISM: Oryza sativa
<220> FEATURE:
<223> OTHER INFORMATION: DNA marker: Lower Primer of M5-At (Hd1)

<400> SEQUENCE: 29
gcaagaaact gatgcggtag                                                       20

<210> SEQ ID NO 30
<211> LENGTH: 20
<212> TYPE: DNA
<213> ORGANISM: Oryza sativa
<220> FEATURE:
<223> OTHER INFORMATION: DNA marker: SNP Primer of M5-At (Hd1)

<400> SEQUENCE: 30
ccaagaggtc tccgcagccg                                                       20
```

CULTIVAR, METHOD FOR DIFFERENTIATING PLANT CULTIVARS, AND METHOD FOR CAUSING EARLIER MATURING OF RICE INDIVIDUAL

CROSS-REFERENCE TO RELATED APPLICATIONS

This application is a National Stage entry of International Application PCT/JP2011/056551 filed Mar. 18, 2011. The disclosure of the prior application is hereby incorporated in its entirety by reference.

SEQUENCE LISTING

The instant application contains a Sequence Listing which has been submitted electronically in ASCII format and is hereby incorporated by reference in its entirety. Said ASCII copy, created on Nov. 27, 2013, is named 107439-00340_SL.txt and is 6,318 bytes in size.

TECHNICAL FIELD

The present invention relates to a new cultivar produced by a non-genetic recombination method, a method for differentiating that new cultivar, and a method for causing early maturing of a rice individual.

The subject seeds for rice cultivar Koshihikari kazusa 6go has the accession number FERM ABP-22175, having been deposited on Jun. 20, 2014. All restrictions upon availability to the public will be irrevocably removed upon granting of a patent.

BACKGROUND ART

A population that belongs to the same species, but differs from other populations in terms of a certain trait as a result of having a different genetic composition, is referred to as a cultivar. In other words, even within the same species of plant, cultivation difficulty, resistance to damage caused by diseases and insects, yield, quality and the like differ according to the particular cultivar. Consequently, in agricultural products and particularly in major crops such as rice, barley or wheat, cultivar improvement has been carried out extensively in order to obtain better cultivars, and in recent years, cultivar improvement has been aggressively implemented by not only nursery companies and other private firms, but also by government agencies at the national and prefectural levels.

Accompanying recent progress made in fields such as nucleic acid analysis technology, the genes of various plants such as thale cress, rice and wheat have been analyzed, and the resulting genetic information has been disclosed. Cultivar improvement consisting of introducing a gene from an introduced species using genetic recombination methods is being carried out extensively by using this disclosed genetic information. For example, Hd1 gene, which encodes a plant-derived protein that has the function of increasing plant photosensitivity, and a method for producing a transgenic plant into which Hd1 gene has been introduced, have been disclosed (see, for example, Patent Document 1). However, although cultivar improvement by genetic recombination has the advantage of being able to introduce a trait possessed by a distantly related species for which crossbreeding is normally not possible, there is the problem of not always being able to adequately verify the safety thereof.

Consequently, new cultivars are being extensively produced by non-genetic recombination methods in the case of edible plants including rice. For example, Patent Document 2 discloses a method for producing a new cultivar having a target trait, without altering preferable traits possessed by the original cultivar, by controlling a substitution region using a chromosome fragment derived from an introduced cultivar in the case of substituting with an exogenous useful chromosome fragment by a non-genetic recombination method. The same Patent Document 2 also describes a new rice cultivar in the form of Koshihikari eichi no. 3 in which only a region containing Habataki Hd1 gene is introduced into Koshihikari by this method for producing a new cultivar.

In rice in particular, Koshihikari is desired that is able to be cultivated over a wider range of regions. Koshihikari has flavor that is superior to that of other cultivars and is preferred by consumers. Consequently, rice farmers cultivate Koshihikari preferentially even in regions that cannot always be said to be suitable for cultivation of Koshihikari. However, in the case of cultivating Koshihikari in southern regions, a satisfactory yield cannot be expected due to the heading time being excessively early. Moreover, flavor ends up decreasing due to persistent high temperatures during the heading time. On the other hand, in the case of cultivating Koshihikari in northern regions, it ends up maturing late, and even if heads have appeared, for example, their ripening is poor due to low temperatures, thereby preventing rice from being harvested.

PRIOR ART DOCUMENTS

Patent Documents

[Patent Document 1] Japanese Patent No. 3660967
[Patent Document 2] Japanese Patent No. 4409610

DISCLOSURE OF THE INVENTION

Problems to be Solved by the Invention

As a result of research conducted by the inventor of the present invention, it was found that Koshihikari is only suitable for cultivation in Japan within the range of 35.5 degrees north latitude to 38.5 degrees north latitude. If there was a cultivar of Koshihikari that could be cultivated even in regions located farther north than 38.5 degrees north latitude, Koshihikari would be able to be harvested even in regions such as Hokkaido where it was previously not possible to cultivate Koshihikari.

An object of the present invention is to provide a new rice cultivar that can be cultivated even in regions located farther to the north than in the past, and a method for causing rice individuals to mature earlier.

Means for Solving the Problems

As a result of conducting extensive studies to solve the aforementioned problems, the inventor of the present invention found that rice cultivar Koshihikari can be caused to mature early enough to allow cultivation even in regions located farther to the north than in the past by substituting a chromosome fragment of a specific region present on the third chromosome of rice cultivar Habataki and a chromosome fragment of a specific region present on the sixth chromosome of rice cultivar Habataki into rice cultivar Koshihikari.

Namely, the present invention provides the following:
(1) a rice cultivar Koshihikari kazusa no. 6 (*Oryza sativa* L. cultivar Koshihikari kazusa no. 6) having the cultivar registration application number 25587;
(2) a progeny individual obtained by crossbreeding two individuals selected from the group consisting of an individual of the cultivar described in (1) above and a progeny individual of the individual of the cultivar described in (1) above;

(3) a method for differentiating rice cultivars: including, determining whether or not a certain rice individual is a specific cultivar, wherein an SNP (single nucleotide polymorphism) corresponding to the 31,521,442$^{nd}$ SNP in the third chromosome of rice cultivar Nipponbare (A in rice cultivar Koshihikari and C in rice cultivar Habataki) is designated as DNA marker M1, an SNP corresponding to the 31,689,690$^{th}$ SNP of the third chromosome of rice cultivar Nipponbare (C in rice cultivar Koshihikari and T in rice cultivar Habataki) is designated as DNA marker M2, an SNP corresponding to the 32,208,924$^{th}$ SNP of the third chromosome of rice cultivar Nipponbare (A in rice cultivar Koshihikari and G in rice cultivar Habataki) is designated as DNA marker M3, an SNP corresponding to the 32,298,686$^{th}$ SNP of the third chromosome of rice cultivar Nipponbare (G in rice cultivar Koshihikari and C in rice cultivar Habataki) is designated as DNA marker M4, an SNP corresponding to the 32,363,157$^{th}$ SNP of the third chromosome of rice cultivar Nipponbare (A in rice cultivar Koshihikari and T in rice cultivar Habataki) is designated as DNA marker M5, one or more DNA markers selected from the group consisting of the DNA markers M1 to M5 is typed by genome analysis of the rice individual, and in the case the resulting typing result coincides with the result for rice cultivar Koshihikari kazusa no. 6 (*Oryza sativa* L. cultivar Koshihikari kazusa no. 6) or rice cultivar Koshihikari eichi no. 5 (*Oryza sativa* L. cultivar Koshihikari eichi no. 5), the rice individual is identified as rice cultivar Koshihikari kazusa no. 6 or rice cultivar Koshihikari eichi no. 5;

(4) a method for differentiating rice cultivars: including, determining whether or not a certain rice individual is a specific cultivar, wherein an SNP corresponding to the 8,757,818$^{th}$ SNP of the sixth chromosome of rice cultivar Nipponbare (C in rice cultivar Koshihikari and T in rice cultivar Habataki) is designated as DNA marker M1, an SNP corresponding to the 8,940,503$^{rd}$ SNP of the sixth chromosome of rice cultivar Nipponbare (A in rice cultivar Koshihikari and G in rice cultivar Habataki) is designated as DNA marker M2, an SNP corresponding to the 9,325,062$^{nd}$ SNP of the sixth chromosome of rice cultivar Nipponbare (C in rice cultivar Koshihikari and G in rice cultivar Habataki) is designated as DNA marker M3, an SNP corresponding to the 9,533,057$^{th}$ SNP of the sixth chromosome of rice cultivar Nipponbare (G in rice cultivar Koshihikari and C in rice cultivar Habataki) is designated as DNA marker M4, an SNP corresponding to the 9,777,196$^{th}$ SNP of the sixth chromosome of rice cultivar Nipponbare (A in rice cultivar Koshihikari and T in rice cultivar Habataki) is designated as DNA marker M5, one or more DNA markers selected from the group consisting of the DNA markers M1 to M5 is typed by genome analysis of the rice individual, and in the case the resulting typing result coincides with the result for rice cultivar Koshihikari kazusa no. 6 (*Oryza sativa* L. cultivar Koshihikari kazusa no. 6) or rice cultivar Koshihikari eichi no. 3 (*Oryza sativa* L. cultivar Koshihikari eichi no. 3), the rice individual is identified as rice cultivar Koshihikari kazusa no. 6 or rice cultivar Koshihikari eichi no. 3;

(5) a method for causing a rice individual to mature earlier, including: replacing a region corresponding to a region containing base number 31,720,064 to base number 31,724,043 of the third chromosome of rice cultivar Nipponbare with a chromosome fragment composed of the corresponding region of rice cultivar Koshihikari kazusa no. 6 or rice cultivar Habataki in the third chromosome of the rice individual;

(6) the method for causing a rice individual to mature earlier described in (5) above, wherein the chromosome fragment is replaced so that the upstream end of the chromosome fragment is present in a region corresponding to a region containing base number 31,689,691 to base number 31,720,064 of the third chromosome of rice cultivar Nipponbare, and the downstream end of the chromosome fragment is present in a region corresponding to a region containing base number 31,724,043 to base number 32,298,685 of the third chromosome of rice cultivar Nipponbare;

(7) a method for causing a rice individual to mature earlier, including: replacing a region corresponding to a region containing base number 31,689,690 to base number 32,298,686 of the third chromosome of rice cultivar Nipponbare with a chromosome fragment composed of the corresponding region of rice cultivar Koshihikari kazusa no. 6 or rice cultivar Habataki in the third chromosome of the rice individual;

(8) the method for causing a rice individual to mature earlier described in (7) above, wherein the chromosome fragment is replaced so that the upstream end of the chromosome fragment is present in a region corresponding to a region containing base number 31,521,443 to base number 31,689,690 of the third chromosome of rice cultivar Nipponbare, and the downstream end of the chromosome fragment is present in a region corresponding to a region containing base number 32,298,686 to base number 32,363,156 of the third chromosome of rice cultivar Nipponbare;

(9) a rice cultivar produced by the method for causing a rice individual to mature earlier described in any of (5) to (8) above;

(10) a progeny individual obtained by crossbreeding two individuals selected from the group consisting of an individual of the cultivar described in (9) above and a progeny individual of the individual of the cultivar described in (9) above; and,

(11) a method for cultivating rice, including: cultivating in a region located farther north than 38.5 degrees north latitude one or more types of rice individuals selected from the group consisting of a rice individual in which a region corresponding to a region containing base number 8,940,503 to base number 9,533,057 of the sixth chromosome of rice cultivar Nipponbare has been replaced with a chromosome fragment composed of the corresponding region of rice cultivar Koshihikari kazusa no. 6, rice cultivar Koshihikari eichi no. 3 or rice cultivar Habataki in the sixth chromosome of the rice individual, a rice individual of rice cultivar Koshihikari kazusa no. 6, and a rice individual of rice cultivar Koshihikari eichi no. 3.

Effects of the Invention

The new cultivar of the present invention in the form of rice cultivar Koshihikari kazusa no. 6 matures much earlier than Koshihikari and can be cultivated and harvested for rice even in regions farther to the north than 38.5 degrees north latitude. In addition, rice cultivar Koshihikari kazusa no. 6 is a new cultivar that has characteristics other than harvesting time, such as quality and yield, that are nearly the same as those of Koshihikari.

Furthermore, the method for differentiating rice cultivars of the present invention can differentiate rice cultivar Koshihikari kazusa no. 6.

In addition, the method for causing early maturing of a rice individual of the present invention can mature a rice individual earlier than the original cultivar.

BRIEF DESCRIPTION OF THE DRAWINGS

FIG. 5 is a drawing schematically representing the genome of Koshihikari eichi no. 3.

FIG. 6 is a drawing showing the results of investigating the heading times of Koshihikari and Koshihikari eichi no. 3 in Chiba prefecture.

FIG. 7 is a drawing showing the results of investigating the heading times of Koshihikari and Koshihikari eichi no. 3 in Hokkaido.

FIG. 9 is a drawing showing the results of investigating the heading time of Koshihikari kazusa no. 6 in Chiba prefecture along with the results for Koshihikari, Koshihikari eichi no. 5 and Koshihikari eichi no. 3.

FIG. 10 is a drawing showing the results of investigating the heading time of Koshihikari kazusa no. 6 in Hokkaido along with the results for Koshihikari, Koshihikari eichi no. 5 and Koshihikari eichi no. 3.

BEST MODE FOR CARRYING OUT THE INVENTION

Figure 1:
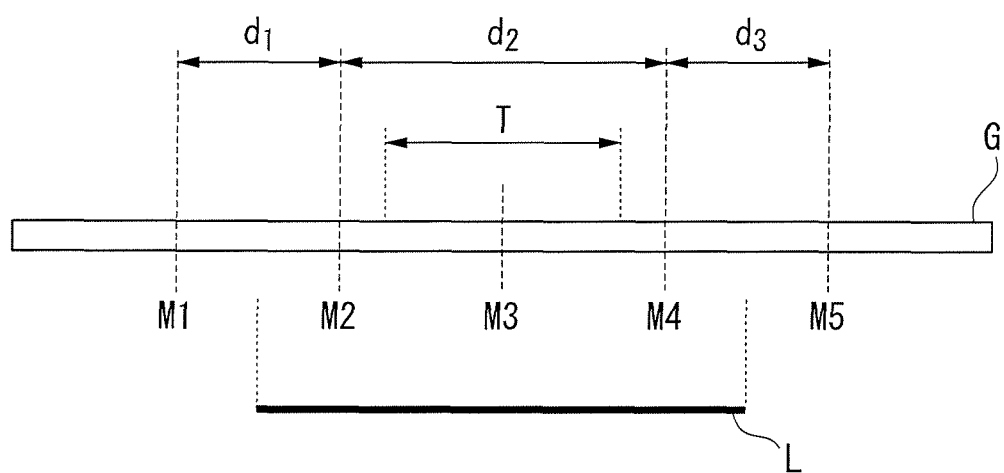
FIG. 1 is a drawing showing a target region T on chromosome G of an original cultivar, a chromosome fragment L derived from an introduced cultivar that has been substituted therein, and DNA markers M1 to M5.

A modified chromosome fragment strain in the present invention refers to a strain in which only a portion of a chromosome of the original cultivar has been replaced with a chromosome fragment derived from an introduced cultivar. Here, there are no particular limitations on the introduced cultivar provided it is a cultivar other than the original cultivar, and may be a cultivar of a plant of the same species as the original cultivar, may be a cultivar of a plant of a different species than the original cultivar, or may be a cultivar other than a plant cultivar such as that of an animal. Furthermore, in the present invention, a cultivar refers to a population that belongs to the same plant species and can be clearly differentiated from other cultivars of the same species in terms of a certain trait as a result of having a different genetic composition.

In the present invention, there are no particular limitations on DNA markers provided they allow the detection of differences in DNA sequences in chromosomes that enables differentiation between a chromosome derived from an original cultivar and a chromosome derived from an introduced cultivar, and DNA markers normally used in the field of genetic analysis can be used. These DNA markers may be markers capable of detecting genetic polymorphisms such as differences in the number of repeats of single nucleotide polymorphisms (SNP) or simple sequence repeats (SSR), or may be restrictive fragment length polymorphism (RFLP) markers. Furthermore, differentiation between an allele derived from an original cultivar and an allele derived from an introduced cultivar by these DNA markers can be carried out in accordance with ordinary methods. For example, each polymorphism can be differentiated by carrying out PCR using DNA extracted from each individual as template and using primers and the like capable of specifically hybridizing with a specific SNP or SSR, and then detecting the presence or absence of the PCR product using electrophoresis and the like. In addition, each polymorphism can be differentiated by treating DNA extracted from each individual with restrictase and then detecting the pattern of a DNA fragment using electrophoresis and the like. Furthermore, primers and the like capable of specifically hybridizing with a specific SNP or SSR can be designed in accordance with ordinary methods using commonly used primer design tools and the like corresponding to the base sequence of the SNP or SSR. In addition, designed primers and the like can be synthesized using any method well known in the relevant technical field.

Known DNA markers can be suitably used for these DNA markers. In addition, these DNA markers may also be newly produced DNA markers. Examples of known DNA markers that can be used in rice include the SNP markers disclosed in International Publication No. WO 2003/070934 and DNA markers publicly disclosed by the Rice Genome Research Program.

Furthermore, genetic information on each cultivar can be acquired from the international base sequence databases of the National Center for Biotechnology Information (NCBI) or the DNA Data Bank of Japan (DDBJ). Genetic information on each rice cultivar in particular can be acquired from the Knowledge-based Oryza Molecular biological Encyclopedia.

In the present invention and description of the present application, a "region from base number X to base number Y of a chromosome of rice cultivar Nipponbare" is a region determined based on the base sequence of genomic DNA of the rice cultivar Nipponbare publicly disclosed by RGB (Version 4: IRGSP-build4-06/04/21).

In addition, in the present invention and description of the present application, a "region corresponding to a region from base number X to base number Y of a chromosome of rice cultivar Nipponbare" is a region in a chromosome of a rice individual that is highly homologous with the corresponding sequence in a chromosome of rice cultivar Nipponbare, and can be determined by aligning the base sequences of known genomic DNA of rice cultivar Nipponbare and genomic DNA of the rice individual so as to demonstrate the highest homology. In addition, an "SNP corresponding to an SNP of rice cultivar Nipponbare" in a rice individual other than rice cultivar Nipponbare refers to a base at a location corresponding to the SNP within a region containing the SNP in the case the base sequences of known genomic DNA of rice cultivar Nipponbare and genomic DNA of the rice individual have been aligned so as to demonstrate the highest homology.

In order to breed a new cultivar that can be cultivated in regions farther north than those of conventional cultivars, the inventor of the present invention first conducted a quantitative trait locus (QTL) analysis of heading time in an isolated population by crossbreeding rice cultivar Habataki and rice cultivar Koshihikari. As a result, a QTL that results in early maturation by advancing heading time was determined to be present in the QTS14 region of the long arm of the third chromosome of rice cultivar Habataki (region corresponding to a region containing base number 31,720,064 to base number 31,724,043 of the third chromosome of rice cultivar Nipponbare). Therefore, the inventor of the present invention produced a new cultivar in which a gene contained in the corresponding region of Koshihikari was replaced with a gene derived from Habataki. The new cultivar was predicted to be rice that matures earlier than the original Koshihikari cultivar.

In the case of carrying out selective plant breeding by a non-genetic recombination method, if the introduced chromosome fragment derived from an introduced cultivar is excessively large, there is the risk of introducing a large number of other genes of indeterminate function other than the gene for the target trait, as well as the risk of impairing preferable traits possessed by the original cultivar. Therefore, the inventor of the present invention produced a new cultivar according to the method described in Patent Document 2 in order to produce a new cultivar having a target trait, without altering preferable traits possessed by the original cultivar, by controlling a substitution region using an introduced chromosome fragment derived from an introduced cultivar.

More specifically, the method used to produce a new cultivar described in Patent Document 2 is as described below. First, five types of DNA markers having the positional relationships shown in FIG. 1 were set based on known rice genetic information. Namely, a DNA marker M2 was set for the upstream end of a target region T or upstream therefrom, a DNA marker M1 was set upstream from DNA marker M2, a DNA marker M4 was set for the downstream end of the target region T or downstream therefrom, a DNA marker M5 was set downstream from the DNA marker M4, and a DNA marker M3 was set within the target region T. Next, back crossbreeding was carried out on a modified chromosome fragment strain in which only a portion of the Koshihikari chromosome containing the target region T was replaced with a chromosome fragment derived from Habataki, and preferable individuals based on the aforementioned five types of DNA markers M1 to M5 were selected from the resulting hybrid population. Subsequently, by suitably similarly repeating selection of preferable individuals based on DNA markers M1 to M5 by carrying out self-crossbreeding or back crossbreeding on the individuals, a progeny individual was able to be obtained such that the upstream end of the region replaced by the Habataki-derived chromosome fragment is present between DNA markers M1 and M2, and the downstream end of that region is present between DNA markers M4 and M5. As shown in FIG. 1, in this progeny individual, DNA markers M1 and M5 are of the same type as the original cultivar, while DNA markers M2, M3 and M4 are of the same type as the introduced cultivar (Habataki in the present invention).

Here, in the method for producing a new cultivar described in Patent Document 2, if a distance d1 between DNA markers M1 and M2 is long, the range over which the upstream end of chromosome fragment L derived from an introduced cultivar (chromosome fragment derived from Habataki in the present application) can be present becomes large, thereby making it difficult to determine the length of the introduced Habataki-derived chromosome fragment L. On the other hand, if the distance d1 is short, the range over which the upstream end of the Habataki-derived chromosome fragment L can be present becomes small, thereby making it easy to determine the length of the introduced Habataki-derived chromosome fragment L. Similarly, if a distance d3 between DNA markers M4 and M5 is long, the range over which the downstream end of the Habataki-derived chromosome fragment L can be present becomes large, thereby making it difficult to determine the length of the introduced Habataki-derived chromosome fragment L, while if the distance d3 is short, the range over which the downstream end of the Habataki-derived chromosome fragment L can be present becomes small, thereby making it easy to determine the length of the introduced Habataki-derived chromosome fragment L.

More specifically, the inventor of the present invention produced a new cultivar according to the method for producing a new cultivar described in Patent Document 2 respectively using the sets of DNA markers M1 to M5 shown in Table 1, namely by using an SNP (single nucleotide polymorphism) corresponding to the $31,521,442^{nd}$ SNP of the third chromosome of rice cultivar Nipponbare (A in rice cultivar Koshihikari and C in rice cultivar Habataki) for DNA marker M1 (DNA Marker M1-Ac (QTS14)), using an SNP corresponding to the $31,689,690^{th}$ SNP of the third chromosome of rice cultivar Nipponbare (C in rice cultivar Koshihikari and T in rice cultivar Habataki) for DNA marker M2 (DNA marker M2-Ct (QTS14)), using an SNP corresponding to the $32,208,924^{th}$ SNP of the third chromosome of rice cultivar Nipponbare (A in rice cultivar Koshihikari and G in rice cultivar Habataki) for DNA marker M3 (DNAmarkerM3-Ag (QTS14)), using an SNP corresponding to the $32,298,686^{th}$ SNP of the third chromosome of rice cultivar Nipponbare (G in rice cultivar Koshihikari and C in rice cultivar Habataki) for DNA marker M4 (DNA marker M4-Gc (QTS14)), and using an SNP corresponding to the $32,363,157^{th}$ SNP of the third chromosome of rice cultivar Nipponbare (A in rice cultivar Koshihikari and T in rice cultivar Habataki) for DNA marker M5 (DNA marker M5-At (QTS14)). On the basis of these results, a new cultivar was produced in which a region containing the region from DNA marker M2-Ct (QTS14) to DNA marker M4-Gc (QTS14) (namely, a region corresponding to a region from base number 31,689,690 to base number 32,298,686 of the third chromosome of rice cultivar Nipponbare) was replaced with a chromosome fragment derived from Habataki in the third chromosome of the rice individual. In this new cultivar, the upstream end of the Habataki-derived chromosome fragment is present in a region that is downstream from DNA marker M1-Ac (QTS14) and extends to DNA marker M2-Ct (QTS14) (namely, a region corresponding to a region from base number 31,521,443 to base number 31,689,690 of the third chromosome of rice cultivar Nipponbare), and the downstream end of the chromosome fragment is present in a region extending from DNA marker M4-Gc (QTS14) to upstream from DNA marker M5-At (QTS14) (namely, a region corresponding to a region containing base number 32,298,686 to base number 32,363,156 of the third chromosome of rice cultivar Nipponbare).

TABLE 1

| Marker | Location in $3^{rd}$ chromosome | Koshihikari type | Habataki type | Sequence | SEQ ID NO: |
|---|---|---|---|---|---|
| M1-Ac (QTS14) | 31,521,442 | A | C | Upper primer: CATTCAGTTCTCTCAACTGC | 1 |
|  |  |  |  | Lower primer: GAGATTTTCGAAGGTTCTTCGC | 2 |
|  |  |  |  | SNP primer: TTCCTAACCCAGCTGTGAT | 3 |

TABLE 1-continued

| Marker | Location in 3rd chromosome | Koshihikari type | Habataki type | Sequence | SEQ ID NO: |
|---|---|---|---|---|---|
| M2-Ct (QTS14) | 31,689,690 | C | T | Upper primer: AAAACAGCCACACCTGATCG | 4 |
| | | | | Lower primer: AACATCCTCTGCTTCCTCAG | 5 |
| | | | | SNP primer: TATCGCTAGCCTCCATTTCT | 6 |
| M3-Tc (QTS14) | 32,208,924 | A | G | Upper primer: GAATGGAATGAGCCATACTCC | 7 |
| | | | | Lower primer: CTGCATCTACACGCTATACC | 8 |
| | | | | SNP primer: GTGATGGAAAAGTTGGAAGTTTGAA | 9 |
| M4-Gc (QTS14) | 32,298,686 | G | C | Upper primer: TCCATCCGATGCAGATATCC | 10 |
| | | | | Lower primer: GTAGTTATGGTACACTCGCAG | 11 |
| | | | | SNP primer: GCTGGGGAAAGTGATTTCATC | 12 |
| M5-At (QTS14) | 32,363,157 | A | T | Upper primer: ACGTGGGGTACAGCACTTTGA | 13 |
| | | | | Lower primer: GTCAGGAAAGTTGGAAGAGG | 14 |
| | | | | SNP primer: GATCTCTGACAATATCAAGAAGCT | 15 |

Figure 2:
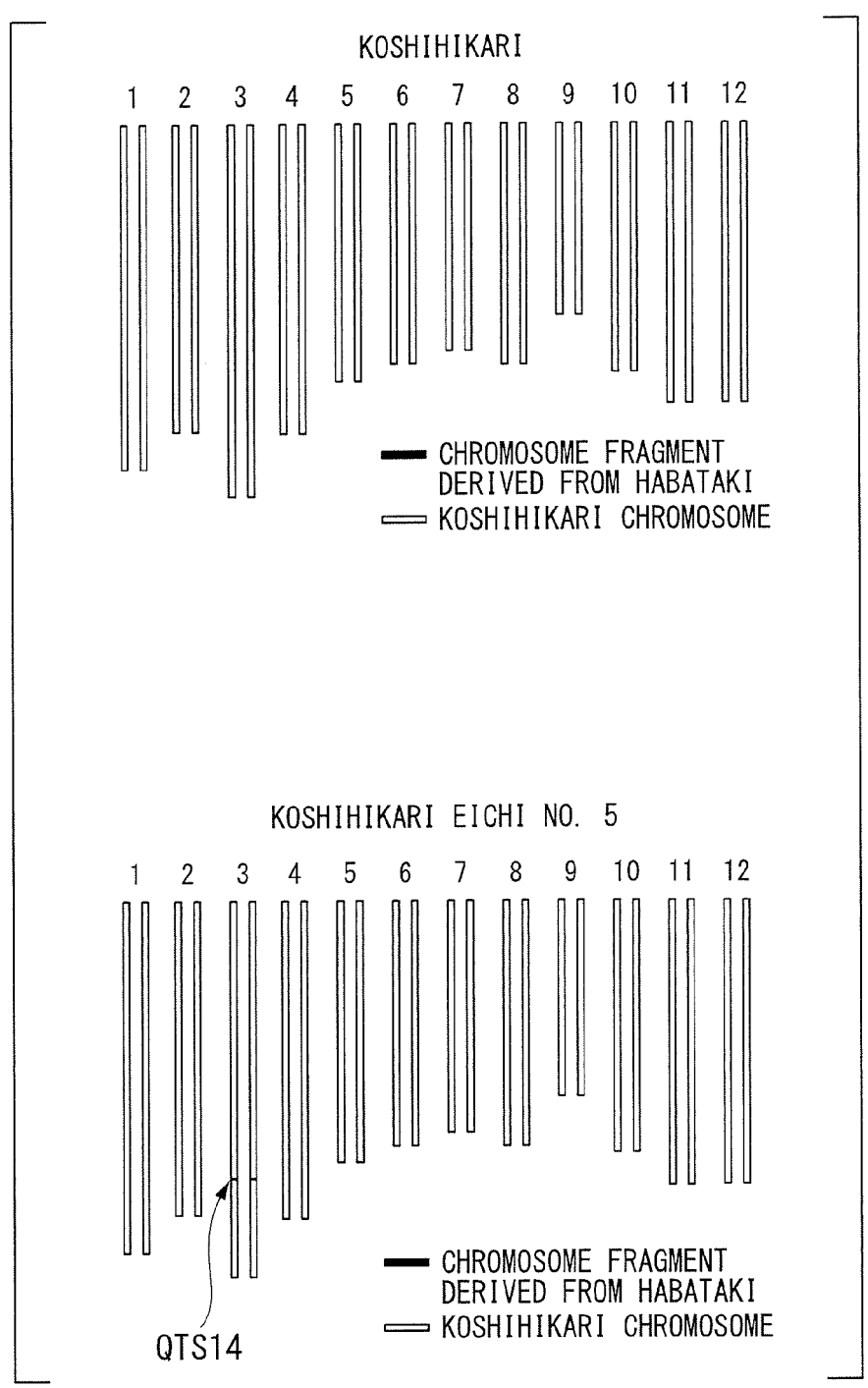
FIG. 2 is a drawing schematically representing the genomes of Koshihikari and Koshihikari eichi no. 5.
Figure 3:
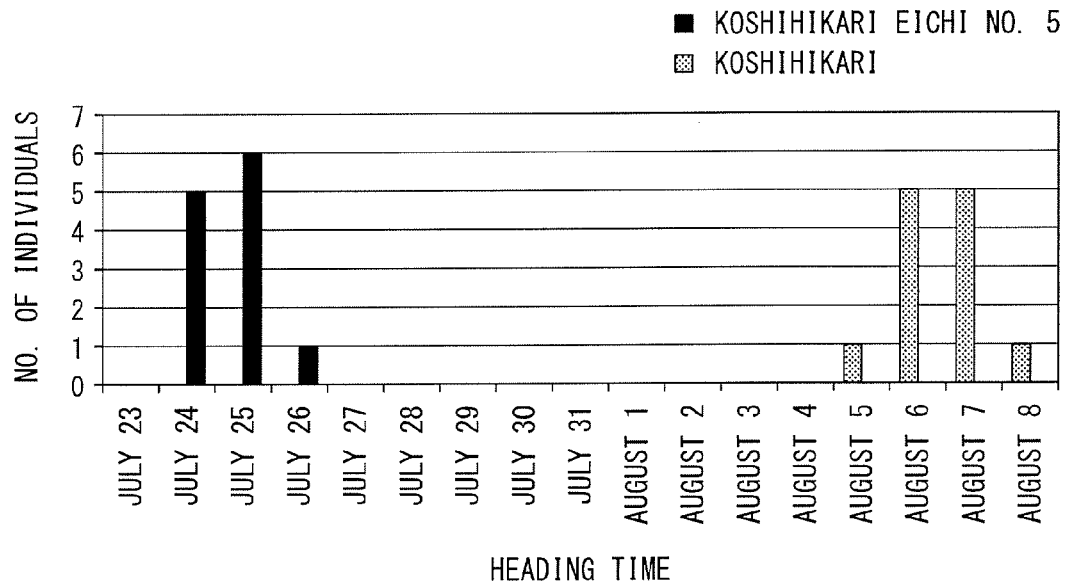
FIG. 3 is a drawing showing the results of investigating the heading times of Koshihikari and Koshihikari eichi no. 5 in Chiba prefecture.

This new cultivar was named "Koshihikari eichi no. 5" by the inventor of the present invention. FIG. 2 is a drawing schematically representing the genomes of Koshihikari and Koshihikari eichi no. 5. When the heading time of Koshihikari eichi no. 5 was measured in a field in Chiba prefecture (seeding date: May 6, 2010, relocation date: Jun. 1, 2010), as shown in FIG. 3, in contrast to the heading time of Koshihikari being from August 5 to August 8, that of Koshihikari eichi no. 5 was from July 24 to July 26. In other words, Koshihikari eichi no. 5 was clearly determined to mature earlier than the original Koshihikari cultivar.

Figure 4:
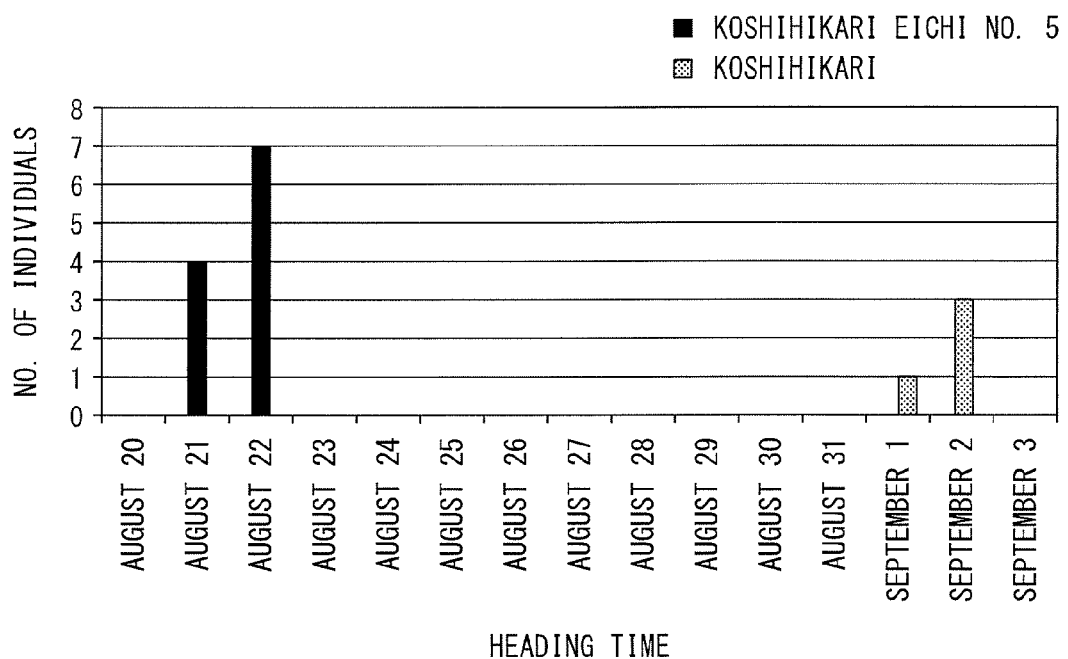
FIG. 4 is a drawing showing the results of investigating the heading times of Koshihikari and Koshihikari eichi no. 5 in Hokkaido.

Moreover, the heading time of Koshihikari eichi no. 5 was measured in a field located in Hokkaido farther north than 38.5 degrees north latitude (seeding date: Apr. 28, 2010, relocation date: Jun. 7, 2010). As a result, as shown in FIG. 4, in contrast to the heading time of Koshihikari being from Sep. 1 to Sep. 2, that of Koshihikari eichi no. 5 was from Aug. 21 to Aug. 22. In other words, even in the case of cultivating in Hokkaido, Koshihikari eichi no. 5 was clearly determined to mature earlier than the original Koshihikari cultivar. However, although the Koshihikari and Koshihikari eichi no. 5 produced heads, they did not mature sufficiently and rice was unable to be harvested.

The inventor of the present invention thought that Koshihikari that matures early enough to allow cultivation even in northern regions could be obtained by further superimposing an introduced chromosome fragment having a function that causes early maturity in Koshihikari eichi no. 5. Therefore, Koshihikari eichi no. 5 was crossbred with rice cultivar Koshihikari eichi no. 3.

Koshihikari eichi no. 3 is a cultivar in which only a region containing the Hd1 gene of the sixth chromosome of the chromosomes of Koshihikari is replaced with a gene fragment derived from Habataki using the method for producing a new cultivar described in Patent Document 2. Table 2 indicates five types of DNA markers used to produce Koshihikari eichi no. 3. DNA marker M1-Ct (also referred as marker M6) is an SNP corresponding to the 8,757,818$^{th}$ SNP of the sixth chromosome of rice cultivar Nipponbare (C in rice cultivar Koshihikari and T in rice cultivar Habataki), DNA marker M2-Ag (also referred as marker M7) is an SNP corresponding to the 8,940,503$^{rd}$ SNP of the sixth chromosome of rice cultivar Nipponbare (A in rice cultivar Koshihikari and G in rice cultivar Habataki), DNA marker M3-Cg (also referred as marker M8) is an SNP corresponding to the 9,325,062$^{nd}$ SNP of the sixth chromosome of rice cultivar Nipponbare (C in rice cultivar Koshihikari and G in rice cultivar Habataki), DNA marker M4-Gc (also referred as marker M9) is an SNP corresponding to 9,533,057$^{th}$ SNP of the sixth chromosome of rice cultivar Nipponbare (G in rice cultivar Koshihikari and C in rice cultivar Habataki), and DNA marker M5-At (also referred as marker M10) is an SNP corresponding to the 9,777,196$^{th}$ SNP of the sixth chromosome of rice cultivar Nipponbare (A in rice cultivar Koshihikari and T in rice cultivar Habataki). Namely, Koshihikari eichi no. 3 is a new cultivar in which a region from DNA marker M2-Ag (Hd1) to DNA marker M4-Gc (Hd1) of the sixth chromosome of rice cultivar Koshihikari (namely, a region corresponding to a region from base number 8,940,503 to base number 9,533,057 of the sixth chromosome of rice cultivar Nipponbare) is replaced with a chromosome fragment derived from Habataki. In this new cultivar, the upstream end of the Habataki-derived chromosome fragment is present in a region that is downstream from DNA marker M1-Ct (Hd1) and extends to DNA marker M2-Ag (Hd1) (namely, a region corresponding to a region from base number 8,757,819 to base number 8,940,503 of the sixth chromosome of rice cultivar Koshihikari), and the downstream end of the chromosome fragment is present in a region extending from DNA marker M4-Gc (Hd1) to upstream from DNA marker M5-At (Hd1) (namely, a region corresponding to a region containing base number 9,533,057 to base number 9,777,195).

TABLE 2

| Marker | Location in 6th chromosome | Koshihikari type | Habataki type | Sequence | SEQ ID NO: |
|---|---|---|---|---|---|
| M1-Ct (Hd1); M6 | 8,757,818 | C | T | Upper primer: GCGAAAAGATGAGGATGTACAC | 16 |
| | | | | Lower primer: CCGTAGGCCTTTGTCAAGTG | 17 |
| | | | | SNP primer: CTTTAATGGTGGCTTATGTC | 18 |

TABLE 2-continued

| Marker | Location in 6th chromosome | Koshihikari type | Habataki type | Sequence | SEQ ID NO: |
|---|---|---|---|---|---|
| M2-Ag (Hd1); M7 | 8,940,503 | A | G | Upper primer: GACCTTCATCTGAGATGTGAC<br>Lower primer: GGAAAGTGAAGCAGCTTCTC<br>SNP primer: CAGCAAGCTCCTGTCCATATTT | 19<br>20<br>21 |
| M3-Cg (Hd1); M8 | 9,325,062 | C | G | Upper primer: AGGCCCTTGTACTGGTAC<br>Lower primer: GTACACAATAGTTGGTGCACC<br>SNP primer: CATGATAAGGTACTCCTGG | 22<br>23<br>24 |
| M4-Gc (Hd1); M9 | 9,325,062 | G | C | Upper primer: GTATCAATCATGTGATCAGTGGC<br>Lower primer: CCTAGGAATTAGGAAGCACAG<br>SNP primer: CAGCCAACATTGAGGGCTCT | 25<br>26<br>27 |
| M5-At (Hd1); M10 | 9,777,196 | A | T | Upper primer: CTTCGTACCATGATGCAGGG<br>Lower primer: GCAAGAAACTGATGCGGTAG<br>SNP primer: CCAAGAGGTCTCCGCAGCCG | 28<br>29<br>30 |

FIG. 5 is a drawing schematically representing the genomes of Koshihikari and Koshihikari eichi no. 3. When the heading time of Koshihikari eichi no. 3 was measured in a field in Chiba prefecture (seeding date: May 6, 2010, relocation date: Jun. 1, 2010), as shown in FIG. 6, in contrast to the heading time of Koshihikari being from Aug. 5 to Aug. 8, that of Koshihikari eichi no. 3 was from Jul. 25 to Jul. 26. In other words, in the case of cultivating in Chiba prefecture, Koshihikari eichi no. 3 matured earlier to about the same degree as Koshihikari eichi no. 5.

Moreover, the heading time of Koshihikari eichi no. 3 was measured in a field located on Hokkaido farther north than 38.5 degrees north latitude (seeding date: Apr. 28, 2010, relocation date: Jun. 7, 2010). As a result, as shown in FIG. 7, the heading time of Koshihikari was from September 1 to September 2, and rice was unable to be harvested. In contrast, the heading time of Koshihikari eichi no. 3 was from August 10 to August 16, and rice was subsequently able to be harvested. In other words, in the case of cultivating in a region located farther north than 38.5 degrees north latitude, Koshihikari eichi no. 3 was clearly able to be cultivated even in Hokkaido since it matures considerably earlier than Koshihikari eichi no. 5. A difference in the degree of early maturation effects resulting from replacing the Hd1 region with a chromosome fragment derived from Habataki depending on the cultivation site, and early maturation effects being greater in the case of cultivating in regions located farther north, such as a region farther north than 38.5 degrees north latitude, than in the case of cultivating in a region where Koshihikari is conventionally cultivated (35.5 degrees to 38.5 degrees north latitude), are findings that were discovered for the first time by the inventor of the present invention.

Figure 8:
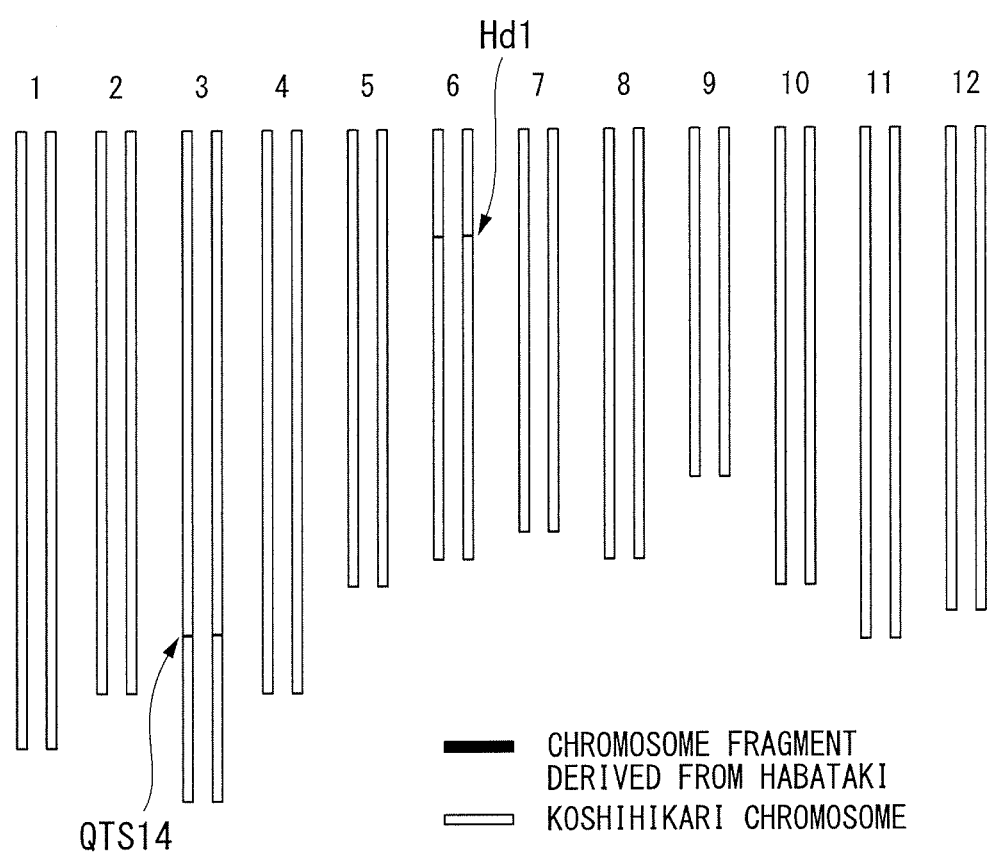
FIG. 8 is a drawing schematically representing the genome of Koshihikari kazusa no. 6.

As is subsequently indicated in Example 1, the inventor of the present invention produced a new cultivar in which only the QTS14 region and Hd1 region in a chromosome of Koshihikari were replaced with chromosome fragments derived from Habataki by crossbreeding Koshihikari eichi no. 5 and Koshihikari eichi no. 3. The inventor of the present invention named this new cultivar "Koshihikari kazusa no. 6". FIG. 8 is a drawing schematically representing the genome of Koshihikari kazusa no. 6. When the heading time of Koshihikari kazusa no. 6 was measured, it was found to mature earlier than Koshihikari eichi no. 3, and rice was able to be harvested even in the case of cultivating in Hokkaido located farther north than 38.5 degrees north latitude. In addition, when the phenotype of Koshihikari kazusa no. 6 was compared with that of Koshihikari, traits other than heading time were roughly the same as those of Koshihikari even in an actual field test.

Koshihikari kazusa no. 6 is a new cultivar that was produced according to the method described in Patent Document 2, and was designed and bred so that 99% or more of the genomic composition thereof is the same as that of Koshihikari. It is a cultivar, which despite maturing early enough so that it can be cultivated even in Hokkaido where Koshihikari has conventionally been unable to be cultivated, is an extremely superior cultivar in that it maintains the flavor and other superior traits possessed by Koshihikari. Therefore, the applicant applied for cultivar registration for Koshihikari kazusa no. 6 as defined in the Seed and Seedlings Law of Japan (Law No. 83, May 29, 1998) (cultivar registration application filing date: Jan. 28, 2011, cultivar registration application number: 25587).

Rice cultivar Koshihikari kazusa no. 6 can be cultivated in accordance with techniques similar to those used for the original Koshihikari cultivar, and rice can be harvested by self-crossbreeding or artificial crossbreeding. In addition, rice cultivar Koshihikari kazusa no. 5 and progeny individuals thereof can be used as parent individuals for developing new cultivars in the same manner as the original Koshihikari cultivar. For example, a new cultivar can be attempted to be developed by crossbreeding a rice cultivar Koshihikari kazusa no. 6 individual with an individual of a different cultivar, and then back crossbreeding the resulting progeny individual with an individual of rice cultivar Koshihikari kazusa no. 6.

In addition, the five types of DNA markers described in Table 1 (DNA marker M1-Ac (QTS14), DNA marker M2-Ct (QTS14), DNA marker M3-Ag (QTS14) and DNA marker M4-Gc (QTS14) compose genomic information unique to rice cultivar Koshihikari kazusa no. 6 and rice cultivar Koshihikari eichi no. 5. Thus, rice cultivar Koshihikari kazusa no. 6 and rice cultivar Koshihikari eichi no. 5 can be differentiated by suitably using these five types of DNA markers.

More specifically, in the case of carrying out a genomic analysis on a rice individual targeted for cultivar differentiation, one or more DNA markers selected from the group consisting of DNA marker M1-Ac (QTS14), DNA marker M2-Ct (QTS14), DNA marker M3-Ag (QTS14), DNA marker M4-Gc (QTS14) and DNA marker M5-At (QTS14) is typed, and the resulting typing result coincides with the result for rice cultivar Koshihikari kazusa no. 6, the rice individual can be determined to be rice cultivar Koshihikari kazusa no. 6 or rice cultivar Koshihikari eichi no. 5.

In addition, the five types of DNA markers described in Table 2 (DNA marker M1-Ct (Hd1), DNA marker M2-Ag (Hd1), DNA marker M3-Cg (Hd1), DNA marker M4-Gc (Hd1) and DNA marker M5-At (Hd1) compose genomic information unique to rice cultivar Koshihikari kazusa no. 6 and Koshihikari eichi no. 3. Thus, rice cultivar Koshihikari kazusa no. 6 and rice cultivar Koshihikari eichi no. 3 can be differentiated by suitably using these five types of DNA markers.

More specifically, in the case of carrying out a genomic analysis on a rice individual targeted for cultivar differentiation, one or more DNA markers selected from the group consisting of DNA marker M1-Ct (Hd1), DNA marker M2-Ag (Hd1), DNA marker M3-Cg (Hd1), DNA marker M4-Gc (Hd1) and DNA marker M5-At (Hd1) is typed, and the resulting typing result coincides with the result for rice cultivar Koshihikari kazusa no. 6, the rice individual can be determined to be rice cultivar Koshihikari kazusa no. 6 or rice cultivar Koshihikari eichi no. 3.

Here, in order to differentiate rice cultivars, all DNA markers M1 to M5 may be used or only several of the five DNA markers may be used. For example, only DNA markers M1 and M2 may be used that serve as recombination points on the upstream side, only DNA markers M4 and M5 may be used that serve as recombination points on the downstream side, or only DNA markers M2 and M4 may be used. Suitably combining a plurality of DNA markers makes it possible to more precisely differentiate rice cultivars.

On the basis of these results, the rice individuals were clearly able to mature earlier than the original cultivar as a result of replacing a QTS14 region in third chromosome of the rice individual, and more specifically, at least a region from DNA marker M2-Ct (QTS14) to DNA marker M4-Gc (QTS14) (namely, a region corresponding to the region containing base number 31,689,690 to base number 32,298,686 of the third chromosome of rice cultivar Nipponbare) with a chromosome fragment composed of the corresponding region of rice cultivar Habataki. Furthermore, since the corresponding regions of rice cultivar Koshihikari kazusa no. 6 and rice cultivar Koshihikari eichi no. 5 are composed of a chromosome fragment composed of the corresponding region of rice cultivar Habataki, they may also be replaced with a chromosome fragment composed of the corresponding region of rice cultivar Koshihikari kazusa no. 6 or rice cultivar Koshihikari eichi no. 5. A rice individual that has been made to mature earlier by introducing a chromosome fragment composed of the corresponding region of rice cultivar Habataki is a cultivar in which the corresponding region has a base sequence that is identical or similar to rice cultivar Koshihikari, and although it is not limited to rice cultivar Koshihikari, in consideration of consumer preferences and the like, it is preferably rice cultivar Koshihikari or a new cultivar produced by using it as a parent cultivar.

In addition, a rice individual can be made to mature earlier than the original cultivar without having significant effects on traits other than heading time by introducing a chromosome fragment into the third chromosome of the rice individual so that the upstream end of the chromosome fragment derived from rice cultivar Habataki (or derived from rice cultivar Koshihikari kazusa no. 6) containing a region from DNA marker M2-Ct (QTS14) to DNAmarkerM4-Gc (QTS14) is present in a region that is downstream from DNA marker M1-Ac (QTS14) and extends to DNA marker M2-Ct (QTS14) (namely, a region corresponding to a region containing base number 31,521,443 to base number 31,689,690 of the third chromosome of rice cultivar Nipponbare), and the downstream end of the chromosome fragment is present in a region extending from DNA marker M4-Gc (QTS14) to upstream from DNA marker M5-At (QTS14) (namely, a region corresponding to a region containing base number 32,298,686 to base number 32,363,156 of the third chromosome of rice cultivar Nipponbare).

In addition, the rice individual can be made to mature considerably earlier to a degree that it can be cultivated even in regions located farther north than 38.5 degrees north latitude by, in addition to the QTS14 region of the third chromosome, further replacing the Hd1 region in the sixth chromosome, and more specifically, at least a region from DNA marker M2-Ag (Hd1) to DNA marker M4-Gc (Hd1) (namely, a region corresponding to a region containing base number 8,940,503 to base number 9,533,057 of the sixth chromosome of rice cultivar Nipponbare) with a chromosome fragment composed of the corresponding region of rice cultivar Habataki. Furthermore, since the corresponding regions of rice cultivar Koshihikari kazusa no. 6 and rice cultivar Koshihikari eichi no. 3 are composed of a chromosome fragment composed of the corresponding region of rice cultivar Habataki, they may also be replaced with a chromosome fragment composed of the corresponding region of rice cultivar Koshihikari kazusa no. 6 or rice cultivar Koshihikari eichi no. 3. A rice individual that has been made to mature earlier by introducing a chromosome fragment composed of the corresponding region of rice cultivar Habataki is a cultivar in which the corresponding region has a base sequence that is identical or similar to rice cultivar Koshihikari, and although it is not limited to rice cultivar Koshihikari, in consideration of consumer preferences and the like, it is preferably rice cultivar Koshihikari or a new cultivar produced by using it as a parent cultivar.

In addition, the rice individual can be made to mature earlier than the original cultivar without having significant effects on traits other than heading time by introducing a chromosome fragment into the sixth chromosome of the rice individual so that the upstream end of the chromosome fragment derived from rice cultivar Habataki (or derived from rice cultivar Koshihikari kazusa no. 6) containing a region from DNA marker M2-Ag (Hd1) to DNA marker M4-Gc (Hd1) is present in a region that is downstream from DNA marker M1-Ct (Hd1) and extends to DNA marker M2-Ag (Hd1) (namely, a region corresponding to a region containing base number 8,757,819 to base number 8,940,503 of the sixth chromosome of rice cultivar Nipponbare), and the downstream end of the chromosome fragment is present in a region extending from DNA marker M4-Gc (Hd1) to upstream from DNA marker M5-At (Hd1) (namely, a region corresponding to a region containing base number 9,533,057 to base number 9,777,195 of the sixth chromosome of rice cultivar Nipponbare).

Furthermore, rice individuals, including Koshihikari eichi no. 3 and Koshihikari kazusa no. 6, in which the Hd1 region of the sixth chromosome (and more specifically, at least a region from DNA marker M2-Ag (Hd1) to DNA marker M4-Gc (Hd1)) is replaced with a chromosome fragment composed of the corresponding region of rice cultivar Habataki can not only be cultivated in regions where Koshihikari is able to be cultivated, but can also be cultivated in regions located farther north than 38.5 degrees north latitude, and enable rice to be harvested in such regions. Although subjected to the effects of air temperature, precipitation and the like, these rice individuals can be cultivated in regions extending from 38.5 degrees to 43.3 degrees north latitude.

On the basis of these studies, Hd1 gene is thought to be the causative gene that is responsible for early maturation in the Hd1 region. On the other hand, when genes contained in the QTS14 region were investigated, a region encoding phytochrome C gene was found to be contained in that region. This gene has been reported to be mainly involved in control of plant flowering time (U.S. Pat. No. 7,566,815). Accordingly, the causative gene responsible for early maturation in the QTS14 region is presumed to be phytochrome C gene. Furthermore, Hd1 gene has been mapped in the region from base number 9,335,337 to base number 9,337,606 of the sixth chromosome in the allele of rice cultivar Nipponbare, while phytochrome C gene has been mapped in the region from base number 31,720,064 to base number 31,724,043 of the third chromosome.

If a region containing the causative gene of early maturation in the Hd1 region and the causative gene of early maturation in the QTS14 region were replaced with a Habataki-derived chromosome fragment, early maturation is thought to be induced in the same manner as in rice cultivar Koshihikari kazusa no. 6 even in the case of a rice individual in which the region was replaced with a chromosome fragment shorter than the Habataki-derived chromosome fragment introduced into Koshihikari kazusa no. 6. Thus, the rice individual is thought to be able to be made to mature earlier than the original cultivar by, for example, replacing a region corresponding to a region containing base number 31,689,691 to base number 31,724,043 of the third chromosome of rice cultivar Nipponbare with a chromosome fragment composed of the corresponding region of rice cultivar Koshihikari kazusa no. 6, rice cultivar Koshihikari eichi no. 5 or rice cultivar Habataki in the third chromosome of the rice individual. In addition, at this time, the rice individual is thought to be able to be made to mature earlier than the original cultivar, without having a significant effect on traits other than heading time, by introducing the chromosome fragment into the third chromosome of the rice individual so that the upstream end of the chromosome fragment is present in a region corresponding to a region containing base number 31,689,690 to base number 31,720,064 of the third chromosome of rice cultivar Nipponbare, and the downstream end of the chromosome fragment is present in a region corresponding to a region containing base number 31,724,043 to base number 32,298,685 of the third chromosome of rice cultivar Nipponbare.

Similarly, the rice individual is thought to be able to be made to mature earlier than the original cultivar by replacing a region corresponding to a region containing base number 9,335,337 to base number 9,337,606 of the sixth chromosome of rice cultivar Nipponbare with a chromosome fragment composed of the corresponding region of rice cultivar Koshihikari kazusa no. 6, rice cultivar Koshihikari eichi no. 3 or rice cultivar Habataki in the sixth chromosome of the rice individual. In addition, at this time, the rice individual is thought to be able to be made to mature earlier than the original cultivar, without having a significant effect on traits other than heading time, by introducing the chromosome fragment into the third chromosome of the rice individual so that the upstream end of the chromosome fragment is present in a region corresponding to a region containing base number 8,940,504 to base number 9,335,337 of the sixth chromosome of rice cultivar Nipponbare, and the downstream end of the chromosome fragment is present in a region corresponding to a region containing base number 9,337,606 to base number 9,533,056 of the third chromosome of rice cultivar Nipponbare.

EXAMPLES

Although the following provides a more detailed explanation of the present invention by indicating examples thereof, the present invention is not limited to the following examples.

Example 1

A new cultivar in which only the QTS14 region and Hd1 region were replaced with a Habataki-derived chromosome fragment in a chromosome of Koshihikari was produced by crossbreeding Koshihikari eichi no. 5 and Koshihikari eichi no. 3.

More specifically, Koshihikari eichi no. 3 and Koshihikari eichi no. 5 were crossbred, two of the resulting progeny individuals (seeds) were cultivated followed by allowing to self-propagate (self-crossbreed) to obtain 100 progeny individuals in the form of seeds. All 100 of these seeds were cultivated, DNA markers in each progeny individual were investigated, and a single cultivated individual was selected in which both DNA marker M3-Cg (Hd1) and DNA marker M3-At (QTS14) were homo chromosome regions of a Habataki-derived allele. The inventor of the present invention named this new cultivar "Koshihikari kazusa no. 5".

The heading time of Koshihikari kazusa no. 6 was measured in a field located in Chiba prefecture (seeding date: May 6, 2010, relocation date: Jun. 1, 2010). The measurement results are shown in FIG. 9 together with the results for Koshihikari, Koshihikari eichi no. 5 and Koshihikari eichi no. 3. In contrast to the heading time of Koshihikari being from August 5 to August 8 and that of Koshihikari eichi no. 5 and Koshihikari eichi no. 3 being from Jul. 24 to Jul. 26, the heading time of Koshihikari kazusa no. 6 was from Jul. 18 to Jul. 23. On the basis of these results, in the case of cultivating in Chiba prefecture, Koshihikari kazusa no. 6 clearly matured earlier than Koshihikari eichi no. 3 and Koshihikari eichi no. 5.

Moreover, the heading time of Koshihikari kazusa no. 6 was also measured in a field located in Hokkaido (43.3 degrees north latitude) (seeding date: Apr. 28, 2010, relocation date: Jun. 7, 2010). The measurement results are shown in FIG. 10 together with the results for Koshihikari, Koshihikari eichi no. 5 and Koshihikari eichi no. 3. In contrast to the heading time of Koshihikari being from Sep. 1 to Sep. 2, that of Koshihikari eichi no. 5 being from Aug. 21 to Aug. 22, and that of Koshihikari eichi no. 3 being from Aug. 10 to Aug. 16, the heading time of Koshihikari kazusa no. 6 was from Aug. 7 to Aug. 9. In addition, in contrast to Koshihikari and Koshihikari eichi no. 5 not maturing, Koshihikari kazusa no. 6 allowed rice to be harvested similar to Koshihikari eichi no. 3. On the basis of these results, Koshihikari kazusa no. 6 clearly was able to be cultivated even in Hokkaido that is farther north than 38.5 degrees north latitude.

A comparative study was conducted between the traits of Koshihikari kazusa no. 6 and Koshihikari (carried out in a field located in Chiba prefecture in 2009). Traits were examined in compliance with an examination of characteristics for application for cultivar registration based on Article 5, Paragraph 1 of the Seed and Seedlings Law of Japan (Law No. 83, 1998). The results of the study are shown in Tables 3 to 6. As a result, Koshihikari kazusa no. 6 matured about 2 weeks earlier than Koshihikari for both heading time and maturation time. In addition, although culm length, length of the major axis of the head and main stem length of Koshihikari kazusa no. 6 were slightly shorter than those of Koshihikari and the number of heads and number of grains on the main stem were also fewer, other traits were basically the same as those of Koshihikari.

TABLE 3

| Stage | Trait | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| | | 1 | 2 | 3 | 4 | 5 | 6 | 7 | 8 | 9 | | Koshihikari | Nipponbare |
| 40 | Leaf: Anthocyanin coloring | None | | | | | | | | | Color 1 | 1 | 1 |
| | Leaf: Anthocyanin color distribution | Tip only | Edges only | Punctate | Entire leaf | | | | | | 1 | 1 | 1 |
| | Leaf: Auricle anthocyanin color | None | | | | | | | | | Color 1 | 1 | 1 |
| 60 | Flag leaf: Orientation of leaf body (initial) | Upright | | Semi-upright | | Horizontal | | Inverted | | | 3 | 3 | 3 |
| 90 | Flag leaf: Orientation of leaf body (later) | Upright | | Semi-upright | — | Horizontal | | Inverted | | | 4 | 4 | 4 |
| 55 | Heading time (50% heading) | Extremely early | | Early | | Medium | | Late | | | 1 July 24 | 3 August 7 | 4 August 19 |
| 65 | Lemma: Apex anthocyanin coloring (initial) | None or extremely light | | Light | | Medium | | Strong | | Very strong | 1 | 1 | 1 |

TABLE 4

| Stage | Trait | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| | | 1 | 2 | 3 | 4 | 5 | 6 | 7 | 8 | 9 | | Koshihikari | Nipponbare |
| 70 | Culm: length (excl. head, excl. floating rice) | Very short | | Short | — | Medium | | Long | | Very long | 4 72.9 m | 6 92.1 cm | 4 74.7 cm |
| | Culm: Node anthocyanin coloring | None | | | | | | | | Color | 1 | 1 | 1 |
| 72-90 | Head: Major axis length | | | Short | | Medium | | Long | | | 3 12.1 cm | 4 14.4 cm | 4 14.2 cm |
| 70 | Head: Number | | | Few | | Medium | | Many | | | 3 6.3 | 4 8.3 | 4 8.8 |
| 70-80 | Head: Awn distribution | Tip only | | Upper half | | Entirety | | | | | 1 | 1 | 1 |
| 60-80 | Spikelet: Amt. of lemma auricles | None or very few | | Few | | Medium | | Many | | Very many | Same as Koshihikari | | |
| 80-90 | Spikelet: Lemma tip color (apiculus color) | White | Yellow | Brown | Red | Violet | Black | | | | 1 | 1 | 1 |
| 90 | Head: Curvature of main axis | Upright | | Tilted | | Hanging | | Curve | | | 5 | 5 | 5 |
| | Head: Shape | Lancet | Fusiform | Rod | Broom | Spread | | | | | 2 | 2 | 2 |
| | Maturation time | Very early | | Early | — | Medium | | Late | | Very late | 4 9/2 | 5 9/17 | 6 9/29 |
| | Lemma color | Yellow-white | Gold | Brown | Reddish violet | Violet | Black | | | | 1 | 1 | 1 |
| | Lemma color: Pattern | None | Gold flutes | Brown flutes | Violet spots | Violet flutes | | | | | 1 | 1 | 1 |

TABLE 5

| | | Cultivar Characteristic Values (Comparison with Standard Cultivar) | | | | | | | | |
|---|---|---|---|---|---|---|---|---|---|---|
| Stage | Trait | 1 | 2 | 3 | 4 | 5 | 6 | 7 | 8 | 9 |
| 92 | Lemma: Apex anthocyanin coloring | None or very light | | Light | | Medium | | Dark | | Very dark |
| | Glume: Length | | | Short | | Medium | | Long | | |
| | Glume: Color | Yellow-white | Gold | Red | Violet | | | | | |
| | Hull: 1000 grain weight (maturity) | | | Small | | Medium | — | Large | | |
| | Hull: Lemma phenol reaction | None | | Light | | Medium | | Dark | | Reacts |
| | Unmilled rice: Length | | | Short | | Medium | | Long | | |
| | Unmilled rice: Width | | | Narrow | | Medium | | Thick | | |
| | Unmilled rice: Shape (from side) | Round | Semi-round | Semi-fusiform | Fusiform | Long fusiform | | | | |
| | Unmilled rice: Color | White | Light brown | Brown spots | Dark brown | Light red | Red | Violet spots | Violet | Dark violet/black |
| | Unmilled rice: Aroma | None or very weak | Weak | Strong | | | | | | |

| Stage | Trait | Comments (measured values) | Characteristics of Control Cultivars | |
|---|---|---|---|---|
| | | | Koshihikari | Nipponbare |
| 92 | Lemma: Apex anthocyanin coloring | 1 | 1 | 1 |
| | Glume: Length | 3 | 3 | 3 |
| | | 1.93 mm | 1.92 mm | 1.92 mm |
| | Glume: Color | 1 | 1 | 1 |
| | Hull: 1000 grain weight (maturity) | 6 | 6 | 7 |
| | | 23.3 g | 23.1 g | 26.4 g |
| | Hull: Lemma phenol reaction | 1 | 1 | 1 |
| | Unmilled rice: Length | 5 | 5 | 6 |
| | | 5.3 mm | 5.2 mm | 5.4 mm |
| | Unmilled rice: Width | 5 | 5 | 5 |
| | | 2.9 mm | 2.9 mm | 2.9 mm |
| | Unmilled rice: Shape (from side) | 2 | 2 | 2 |
| | | 1.8 mm | 1.8 mm | 1.9 mm |
| | Unmilled rice: Color | 2 | 2 | 2 |
| | Unmilled rice: Aroma | 1 | 1 | 1 |

TABLE 6

| | | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| Stage | Trait | 1 | 2 | 3 | 4 | 5 | 6 | 7 | 8 | 9 | | Koshihikari | Nipponbare |
| GIII | No of grains on the main stem | Very few | | Few | — | Medium | | Many | | Very many | 4 / 127 | 5 / 151 | 4 / 123 |
| | Main stem 1st internode length | Very short | | Short | | Medium | | Long | | Very long | 7 / 30.2 cm | 8 / 36.6 cm | 8 / 36.1 cm |
| | Main stem 2nd internode length | Very short | | Short | | Medium | | Long | | Very long | 5 / 17.5 cm | 6 / 22.5 cm | 5 / 17.9 cm |
| | Main stem 3rd internode length | Very short | | Short | | Medium | | Long | | Very long | 5 / 14.4 cm | 6 / 18.0 cm | 4 / 11.1 cm |
| | Main stem 4th internode length | Very short | | Short | | Medium | — | Long | | Very long | 6 / 7.4 cm | 7 / 10.5 cm | 5 / 7.5 cm |
| | Main stem 5th internode length | Very short | | Short | — | Medium | | Long | | Very long | 4 / 7.4 cm | 4 / 3.9 cm | 3 / 2.0 cm |

TABLE 6-continued

| Stage | Trait | Cultivar Characteristic Values (Comparison with Standard Cultivar) | | | | | | | | | Comments (measured values) | Characteristics of Control Cultivars | |
|---|---|---|---|---|---|---|---|---|---|---|---|---|---|
| | | 1 | 2 | 3 | 4 | 5 | 6 | 7 | 8 | 9 | | Koshihikari | Nipponbare |
| | Main stem 6$^{th}$ internode length | Very short | | Short | | Medium | | Long | | Very long | — | — | — |
| | Main stem hull thickness | Very thin | | Thin | | Medium | | Thick | | Very thick | 5<br>2.23 mm | 5<br>2.24 mm | 5<br>2.24 mm |
| | Main stem hull length | Very short | | Short | | Medium | | Long | | Very long | 3<br>7.35 mm | 3<br>7.39 mm | 3<br>7.69 mm |
| | Main stem hull width | Very narrow | | Narrow | | Medium | | Wide | | Very wide | 5<br>3.33 mm | 5<br>3.29 mm | 5<br>3.43 mm |

Industrial Applicability

Since the new cultivar of the present invention in the form of rice cultivar Koshihikari kazusa no. 6 has characteristics that are nearly the same as those of Koshihikari and can be cultivated in regions farther to the north than in the past, it can be used in the field of agriculture in particular. In addition, according to the method of the present invention for causing rice individuals to mature earlier, since rice individuals can be made to mature earlier than the original cultivar, this method can be used in the field of plant breeding in particular.

[Sequence Listing]

The invention claimed is:

1. A rice cultivar, wherein in a chromosome of rice cultivar Koshihikari,
a region corresponding to a region containing base number 31,689,690 to base number 32,298,686 in a third chromosome of rice cultivar Nipponbare is homo-replaced with a chromosome fragment composed of a corresponding region of rice cultivar Habataki in a third chromosome of a rice individual, and an upstream end of the chromosome fragment is present in a region corresponding to a region containing base number 31,521,443 to base number 31,689,690 of the third chromosome of rice cultivar Nipponbare and a downstream end of the chromosome fragment is present in a region corresponding to a region containing base number 32,298,686 to base number 32,363,156 of the third chromosome of rice cultivar Nipponbare,
a single nucleotide polymorphism (SNP) corresponding to the $31,521,442^{nd}$ SNP in the third chromosome of rice cultivar Nipponbare, adenine (A) in rice cultivar Koshihikari and cytosine (C) in a rice cultivar Habataki, is designated as DNA marker M1,
an SNP corresponding to the $31,689,690^{th}$ SNP of the third chromosome of rice cultivar Nipponbare, C in rice cultivar Koshihikari and thymine (T) in rice cultivar Habataki, is designated as DNA marker M2,
an SNP corresponding to the $32,208,924^{th}$ SNP of the third chromosome of rice cultivar Nipponbare, A in rice cultivar Koshihikari and guanine (G) in rice cultivar Habataki, is designated as DNA marker M3,
an SNP corresponding to the $32,298,686^{th}$ SNP of the third chromosome of rice cultivar Nipponbare, G in rice cultivar Koshihikari and C in rice cultivar Habataki, is designated as DNA marker M4,
an SNP corresponding to the $32,363,157^{th}$ SNP of the third chromosome of rice cultivar Nipponbare, A in rice cultivar Koshihikari and T in rice cultivar Habataki, is designated as DNA marker M5, and
the DNA markers M1 to M5 are typed by genome analysis of the rice individual, and
the resulting typing result is such that the DNA marker M1 is A, the DNA marker M2 is T, the DNA marker M3 is G, the DNA marker M4 is C and DNA marker M5 is A,
a region corresponding to a region containing base number 8,940,503 to base number 9,533,057 in a sixth chromosome of rice cultivar Nipponbare is homo-replaced with a chromosome fragment composed of a corresponding region of rice cultivar Habataki in a sixth chromosome of a rice individual, and an upstream end of the chromosome fragment is present in a region corresponding to a region containing base number 8,757,819 to base number 8,940,503 of the sixth chromosome of rice cultivar Nipponbare and the downstream end of the chromosome fragment is present in a region corresponding to a region containing base number 9,533,057 to base number 9,777,195 of the sixth chromosome of rice cultivar Nipponbare, and
an SNP corresponding to the $8,757,818^{th}$ SNP of the sixth chromosome of rice cultivar Nipponbare, C in rice cultivar Koshihikari and T in rice cultivar Habataki, is designated as DNA marker M6,
an SNP corresponding to the $8,940,503^{rd}$ SNP of the sixth chromosome of rice cultivar Nipponbare, A in rice cultivar Koshihikari and G in rice cultivar Habataki, is designated as DNA marker M7,
an SNP corresponding to the $9,325,062^{nd}$ SNP of the sixth chromosome of rice cultivar Nipponbare, C in rice cultivar Koshihikari and G in rice cultivar Habataki, is designated as DNA marker M8,
an SNP corresponding to the $9,533,057^{th}$ SNP of the sixth chromosome of rice cultivar Nipponbare, G in rice cultivar Koshihikari and C in rice cultivar Habataki, is designated as DNA marker M9,
an SNP corresponding to the $9,777,196^{th}$ SNP of the sixth chromosome of rice cultivar Nipponbare, A in rice cultivar Koshihikari and T in rice cultivar Habataki, is designated as DNA marker M10,
the DNA markers M6 to M10 are typed by genome analysis of the rice individual, and
the resulting typing result is such that the DNA marker M6 is C, the DNA marker M7 is G, the DNA marker M8 is G, the DNA marker M9 is C and the DNA marker M10 is A; wherein the rice cultivar is Koshihikari Kazusa no. 6 go, sample of seed of said cultivar is deposited under Accession No. FERM ABP-22175.

2. A method for differentiating rice cultivars: comprising, determining whether or not a certain rice individual is a specific cultivar, wherein
a single nucleotide polymorphism (SNP) corresponding to the $31,521,442^{nd}$ SNP in the third chromosome of rice cultivar Nipponbare, adenine (A) in rice cultivar Koshihikari and cytosine (C) in rice cultivar Habataki, is designated as DNA marker M1,
an SNP corresponding to the $31,689,690^{th}$ SNP of the third chromosome of rice cultivar Nipponbare, C in rice cultivar Koshihikari and thymine (T) in rice cultivar Habataki is designated as DNA marker M2,
an SNP corresponding to the $32,208,924^{th}$ SNP of the third chromosome of rice cultivar Nipponbare, A in rice cultivar Koshihikari and guanine (G) in rice cultivar Habataki is designated as DNA marker M3,
an SNP corresponding to the $32,298,686^{th}$ SNP of the third chromosome of rice cultivar Nipponbare , G in rice cultivar Koshihikari and C in rice cultivar Habataki is designated as DNA marker M4,
an SNP corresponding to the $32,363,157^{th}$ SNP of the third chromosome of rice cultivar Nipponbare, A in rice cultivar Koshihikari and T in rice cultivar Habataki is designated as DNA marker M5,
the DNA markers M1 to M5 is typed by genome analysis of the rice individual, and
in the case the resulting typing result is such that the DNA marker M1 is A, the DNA marker M2 is T, the DNA marker M3 is G, the DNA marker M4 is C and the DNA marker M5 is A, the rice individual is identified as rice cultivar Koshihikari kazusa no. 6 or rice cultivar Koshihikari eichi no. 5, sample of seed of said cultivar is deposited under Accession No. FERM ABP-22175 or Accession No. FERM ABP-22276, respectively.

3. A method for differentiating rice cultivars: comprising, determining whether or not a certain rice individual is a specific cultivar, wherein
an SNP corresponding to the $8,757,818^{th}$ SNP of the sixth chromosome of rice cultivar Nipponbare, cytosine (C) in rice cultivar Koshihikari and thymine (T) in rice cultivar Habataki is designated as DNA marker M1,
an SNP corresponding to the $8,940,503^{rd}$ SNP of the sixth chromosome of rice cultivar Nipponbare, adenine (A) in rice cultivar Koshihikari and guanine (G) in rice cultivar Habataki, is designated as DNA marker M2,
an SNP corresponding to the $9,325,062^{nd}$ SNP of the sixth chromosome of rice cultivar Nipponbare, C in rice cultivar Koshihikari and G in rice cultivar Habataki, is designated as DNA marker M3, an SNP corresponding to the 9,533,057$^{th}$ SNP of the sixth chromosome of rice cultivar Nipponbare, G in rice cultivar Koshihikari and C in rice cultivar Habataki, is designated as DNA marker M4, an SNP corresponding to the 9,777,196$^{th}$ SNP of the sixth chromosome of rice cultivar Nipponbare, A in rice cultivar Koshihikari and T in rice cultivar Habataki, is designated as DNA marker M5, the DNA markers M1 to M5 is typed by genome analysis of the rice individual, and in the case the resulting typing result is such that the DNA marker M1 is C, the DNA marker M2 is G, the DNA marker M3 is G, the DNA marker M4 is C and the DNA marker M5 is A, the rice individual is identified as rice cultivar Koshihikari kazusa no. 6, sample of seed of said cultivar is deposited under Accession No. FERM ABP-22175.

4. A method for causing a rice individual to mature earlier than original cultivar, comprising: homo-replacing a region corresponding to a region containing base number 31,720,064 to base number 31,724,043 of the third chromosome of rice cultivar Nipponbare with a chromosome fragment composed of the corresponding region of the rice cultivar according to claim 1 in the third chromosome of the rice individual.

5. The method for causing a rice individual to mature earlier than original cultivar according to claim 4, wherein the chromosome fragment is replaced so that the upstream end of the chromosome fragment is present in a region corresponding to a region containing base number 31,689,691 to base number 31,720,064 of the third chromosome of rice cultivar Nipponbare, and the downstream end of the chromosome fragment is present in a region corresponding to a region containing base number 31,724,043 to base number 32,298,685 of the third chromosome of rice cultivar Nipponbare.

6. A method for causing a rice individual to mature earlier than original cultivar, comprising: homo-replacing a region corresponding to a region containing base number 31,689,690 to base number 32,298,686 of the third chromosome of rice cultivar Nipponbare with a chromosome fragment composed of the corresponding region of the rice cultivar according to claim 1 or rice cultivar Habataki in the third chromosome of the rice individual.

7. The method for causing a rice individual to mature earlier than original cultivar according to claim 6, wherein the chromosome fragment is replaced so that the upstream end of the chromosome fragment is present in a region corresponding to a region containing base number 31,521,443 to base number 31,689,690 of the third chromosome of rice cultivar Nipponbare, and the downstream end of the chromosome fragment is present in a region corresponding to a region containing base number 32,298,686 to base number 32,363,156 of the third chromosome of rice cultivar Nipponbare.

8. A method for cultivating rice, comprising: cultivating in a region located farther north than 38.5 degrees north latitude one or more types of rice individuals selected from the group consisting of a rice individual in which a region corresponding to a region containing base number 8,940,503 to base number 9,533,057 of the sixth chromosome of rice cultivar Nipponbare has been homo-replaced with a chromosome fragment composed of the corresponding region of the rice cultivar according to claim 1 or rice cultivar Habataki in the sixth chromosome of the rice individual.

* * * * *